US011426063B2

(12) United States Patent
Hsu

(10) Patent No.: US 11,426,063 B2
(45) Date of Patent: Aug. 30, 2022

(54) TONGUE ANTERIORIZER

(71) Applicant: Tzu-Li Hsu, Princeton, NJ (US)

(72) Inventor: Tzu-Li Hsu, Princeton, NJ (US)

( * ) Notice: Subject to any disclaimer, the term of this patent is extended or adjusted under 35 U.S.C. 154(b) by 227 days.

(21) Appl. No.: 16/740,947

(22) Filed: Jan. 13, 2020

(65) Prior Publication Data

US 2020/0146544 A1    May 14, 2020

Related U.S. Application Data

(63) Continuation-in-part of application No. 15/149,468, filed on May 9, 2016, now Pat. No. 10,561,406.

(51) Int. Cl.
*A61B 1/24* (2006.01)
*A61B 1/00* (2006.01)
*A61B 1/267* (2006.01)

(52) U.S. Cl.
CPC ............ *A61B 1/24* (2013.01); *A61B 1/00147* (2013.01); *A61B 1/267* (2013.01)

(58) Field of Classification Search
CPC ......... A61B 13/00; A61B 1/267; A61B 17/02; A61B 90/30
See application file for complete search history.

(56) References Cited

U.S. PATENT DOCUMENTS

| | | | |
|---|---|---|---|
| 4,610,243 A | 9/1986 | Ray | |
| 4,616,633 A * | 10/1986 | Vargas Garcia | ....... A61B 17/02 600/206 |
| 5,406,941 A | 4/1995 | Roberts | |
| 5,467,763 A | 11/1995 | McMahon et al. | |
| 5,667,481 A | 9/1997 | Villalta et al. | |
| 5,743,853 A | 4/1998 | Lauderdale | |
| 6,003,510 A | 12/1999 | Anunta | |
| 6,045,499 A | 4/2000 | Pitesky | |
| 6,901,928 B2 | 6/2005 | Loubser | |
| 8,784,101 B1 * | 7/2014 | Engeron | ................... A61C 5/90 600/242 |
| 9,198,738 B2 * | 12/2015 | Gordon | ................... A61B 13/00 |
| 10,561,406 B2 * | 2/2020 | Hsu | ......................... A61B 1/24 |
| 2001/0034474 A1 | 10/2001 | Ryan | |
| 2007/0289591 A1 * | 12/2007 | Clayton | ............ A61M 16/0488 128/207.14 |
| 2012/0271118 A1 | 10/2012 | White | |

FOREIGN PATENT DOCUMENTS

| | | |
|---|---|---|
| CN | 201710390 | 1/2011 |
| CN | 201782778 | 4/2011 |
| WO | 0030707 | 6/2000 |
| WO | 2011141751 | 11/2011 |
| WO | 2013036891 | 3/2013 |

OTHER PUBLICATIONS

European Search Report, European Patent Application No. 16 81 5084, dated Jan. 23, 2019, 7 pages.

* cited by examiner

*Primary Examiner* — Christopher J Beccia
(74) *Attorney, Agent, or Firm* — Ware, Fressola, Maguire & Barber LLP

(57) ABSTRACT

A tongue anteriorizer includes a handle and a tongue lifting part having a curved portion. The tongue lifting part is configured to move the tongue anteriorly, open the laryngopharyngeal area, and make endotracheal intubation simple, safe and efficient. The tongue lifting part has a wider section and may have protrusions on part of the tongue lifting part surface.

14 Claims, 31 Drawing Sheets

TONGUE ANTERIORIZER

CROSS-REFERENCE TO RELATED APPLICATIONS

This application is a continuation-in-part of a pending U.S. patent application Ser. No. 15/149,468 entitled "TONGUE ANTERIORIZER AND METHOD OF OPERATING SAME" filed May 9, 2016, which is incorporated by reference by its entirety.

BACKGROUND OF THE INVENTION

1. Field of the Invention

The invention relates to medical devices and more particularly to a tongue anteriorizer capable of moving the tongue anteriorly and then lifting it to open the laryngopharyngeal space for upper airway management, and a method of operating same.

2. Description of Related Art

Endotracheal intubation is the process of inserting the endotracheal tube into the trachea. It is the most important procedure for general anesthesia and respiratory resuscitation. Because of variance in oral anatomy, it can be very difficult to do and become "difficult intubation." When that happens, it may cause damage to the airway. If it failed completely, the patient will be in a disaster situation.

There are four groups of medical device for endotracheal intubation, namely, laryngoscope, video laryngoscope, video stylet, and fiberoptic scope.

Laryngoscope is the most common device used for endotracheal intubation. After inserting it into the mouth, it pushes the tongue and mandible forward at about 45-degree angle to open the temporomandibular joint (TMJ) and the laryngopharyngeal space. However, this method is not easy to use on small chin, big tongue, and obese patient because the open space in the oral cavity is small, and it is not easy for laryngoscope to have enough space to work efficiently. For experienced physicians, the success rate for endotracheal intubation is about 90 to 95%. Further, endotracheal intubation failure may injure tissues of the mouth, or even causes the life of a patient.

Video laryngoscope improves on the laryngoscope by adding the video camera. It provides better visibility but does not solve the problems of the laryngoscope.

Video stylet is inside the endotracheal tube and is guided forward by its video image. Because it does not have functionality to open the space, the secretion of the mouth can make it very difficult to see. Pushing it forward, it may move the tongue together and change the normal anatomy around the larynx. When this happens, it is very easy to be disoriented and fails the intubation.

The diameter of fiberoptic scope is smaller and it has a suction function. Its success rate is the best among all intubation devices. However, the learning period is long, and it is time consuming, i.e., very often it will take more than one try to finish the procedure. It is also expensive and easily damaged.

All the problems from the above intubation devices come from not able to open the oral airway properly. Thus, the need for improvement still exists.

SUMMARY OF THE INVENTION

It is an aspect of the present invention to provide a tongue anteriorizer comprising:

a handle;

a connecting part having a first connecting end and a second connecting end, the first connecting end formed with the handle, the connecting part having a connecting part width, and a tongue lifting part including an arc member having a first member end and a second open end, the first member end formed with the second connecting end of the connecting part, wherein the arc member comprises a wider section having a section width greater than the connecting part width.

According to an embodiment of the present invention, the section width of the wider section is smaller than twice the connecting part width.

According to an embodiment of the present invention, the second connecting end of the connecting part comprises a curve oriented in a direction opposite to a curved direction of the arc member of the tongue lifting part.

According to an embodiment of the present invention, a curved length of the connecting part is less than one-third of a curved length of the arc member.

According to an embodiment of the present invention, the tongue anteriorizer is made of a flat plate-like strip having a uniform thickness bent only in one direction.

According to an embodiment of the present invention, the wider section of the arc member has a plurality of protrusions.

According to an embodiment of the present invention, the wider section is near the second open end of the arc member.

According to an embodiment of the present invention, the wider section extends from the second open end to the first member end of the arc member.

According to an embodiment of the present invention, the protrusions are provided only near the second open end of the arc member.

According to an embodiment of the present invention, the protrusions are provided on wider section from the second open end to the first member of the arc member.

According to an embodiment of the present invention, the wider section of the arc member is near the second open end of the arc member, the arc member further having a narrower section narrower than the wider section, the narrower section extends from the wider section to the first member of the arc member, the narrower section having a width smaller than the connecting part width.

According to an embodiment of the present invention, the wider section of the arc member is near the second open end of the arc member, the arc member further having a narrower section narrower than the wider section, the narrower section extends from the wider section to the first member of the arc member, the narrower section having a width equal to the connecting part width.

According to an embodiment of the present invention, the handle has a first handle end and a second handle end, the first handle end having a curved section and the second handle end formed with the second connecting end of the connecting part.

DETAILED DESCRIPTION OF THE INVENTION

Figure 1:
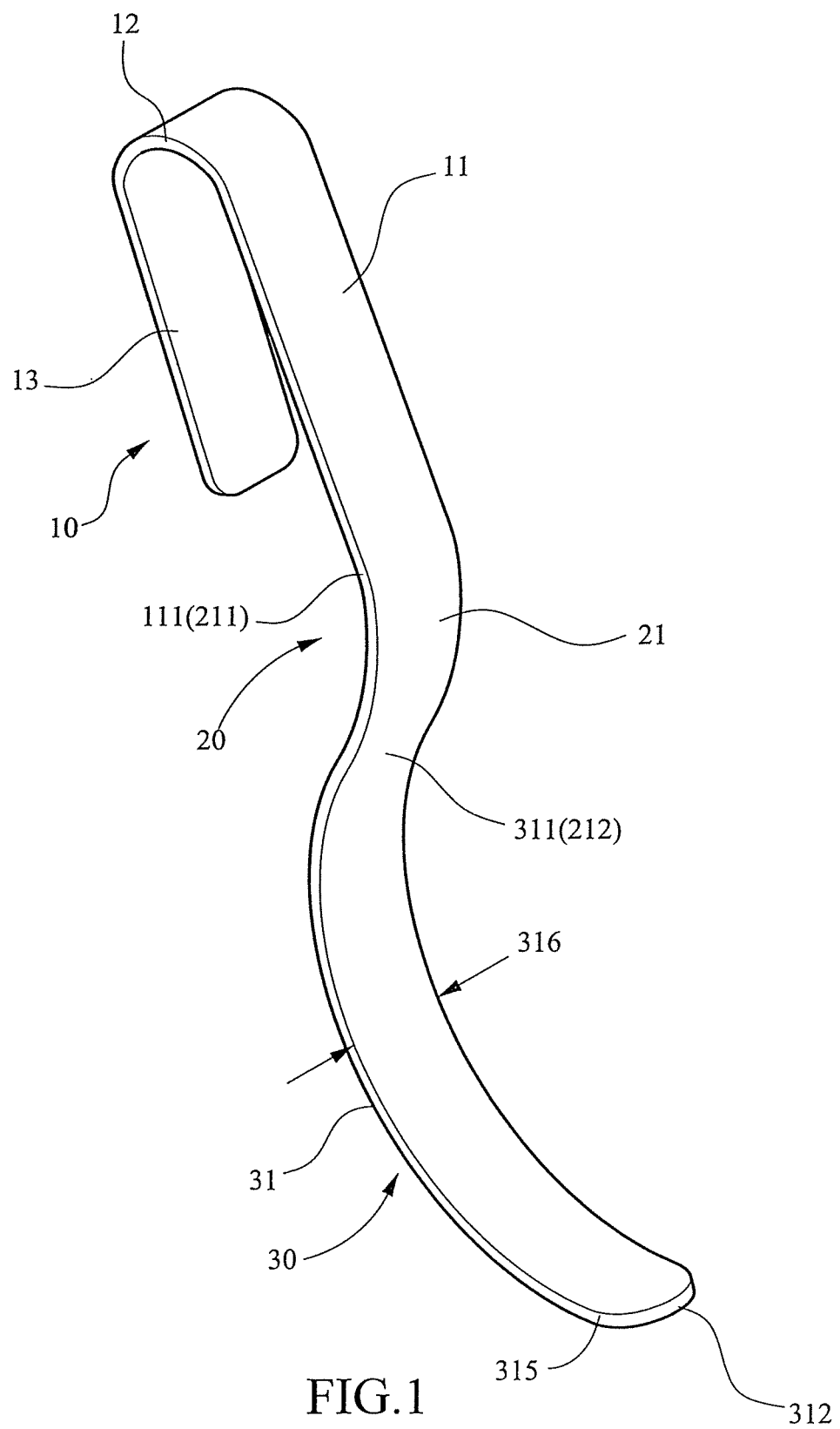
FIG. 1 is a perspective view of a tongue anteriorizer according to a first preferred embodiment of the invention.

Referring to FIG. 1, a tongue anteriorizer in accordance with the invention comprises a handle 10, a connecting part 20, and a tongue lifting part 30 as discussed in detail below.

Figure 2:
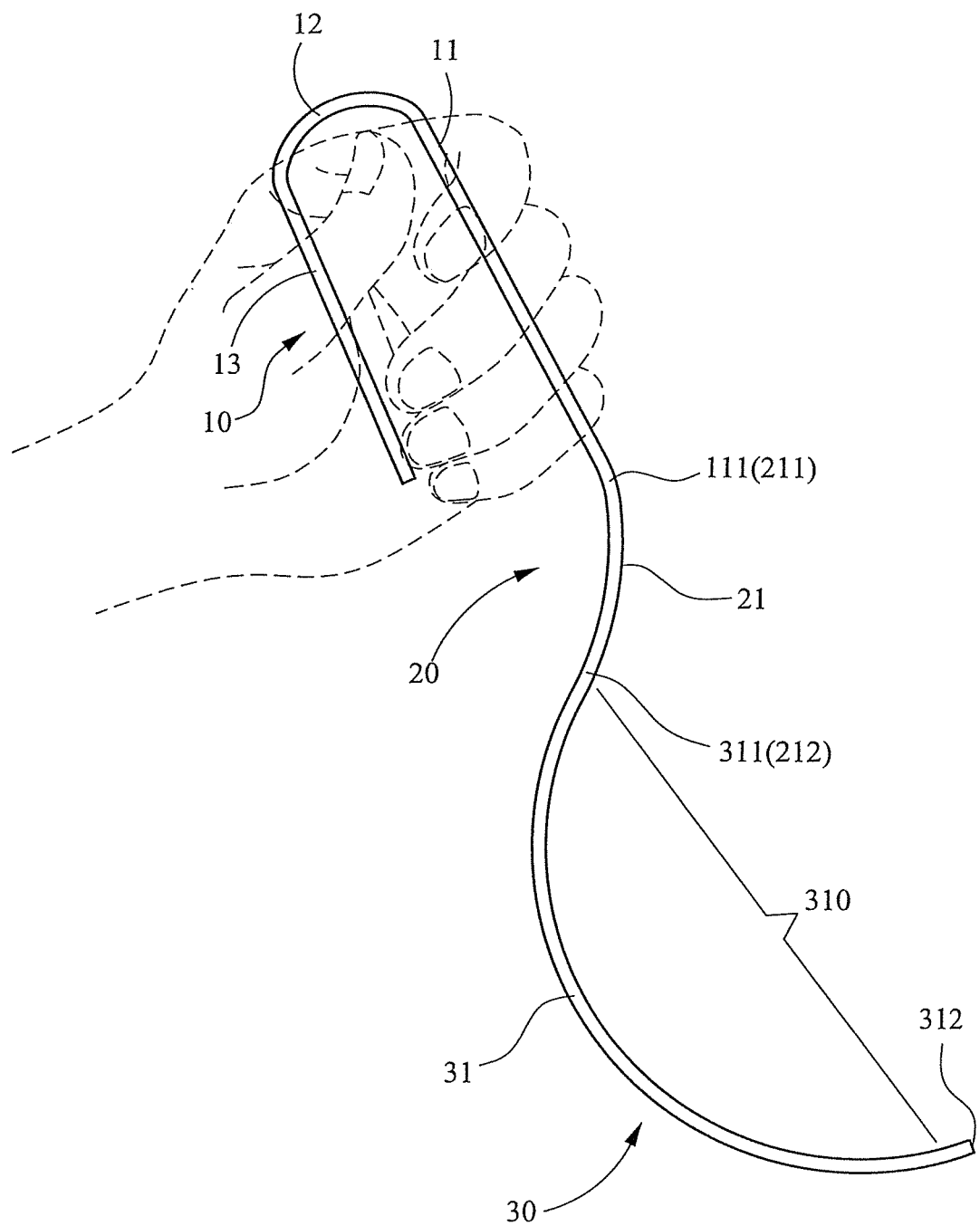
FIG. 2 is a side elevation of the tongue anteriorizer.
Figure 3A:
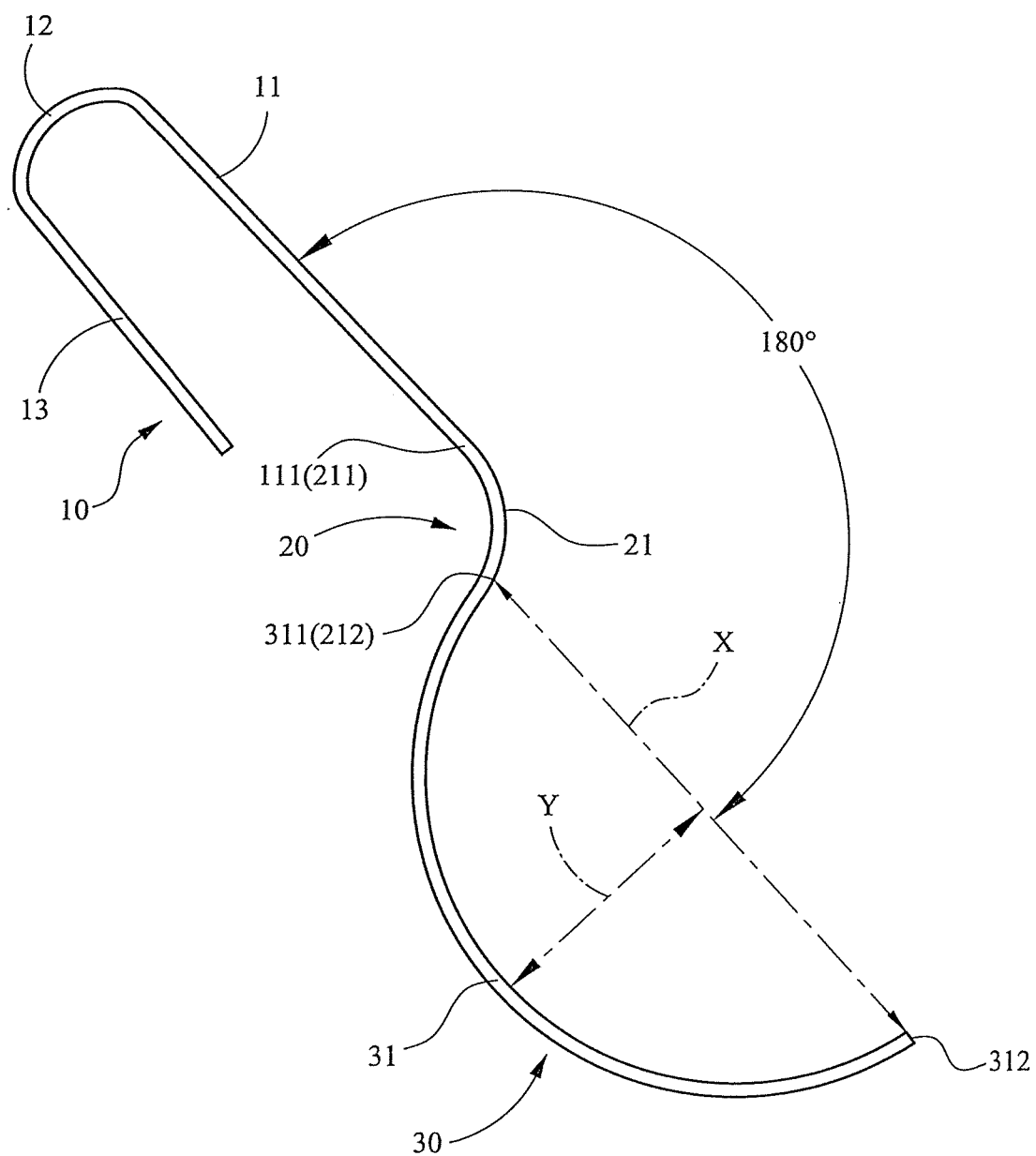
FIG. 3A is a side elevation view of a first aspect of the first preferred embodiment of the invention illustrating the tongue anteriorizer made in a predetermined shape of 180-degree.
Figure 3B:
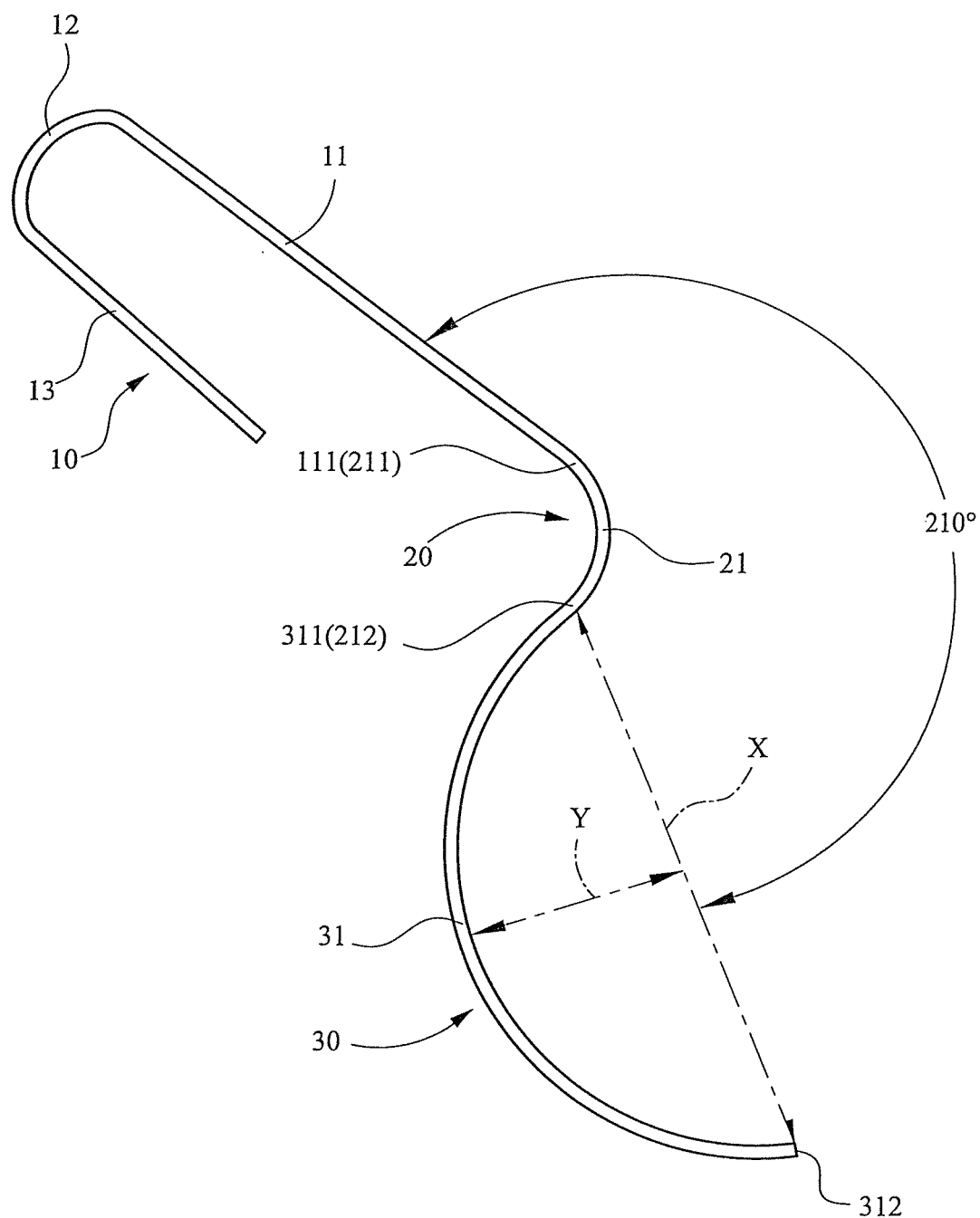
FIG. 3B is a side elevation view of a second aspect of the same illustrating the tongue anteriorizer made in a predetermined shape of 210-degree.
Figure 3C:
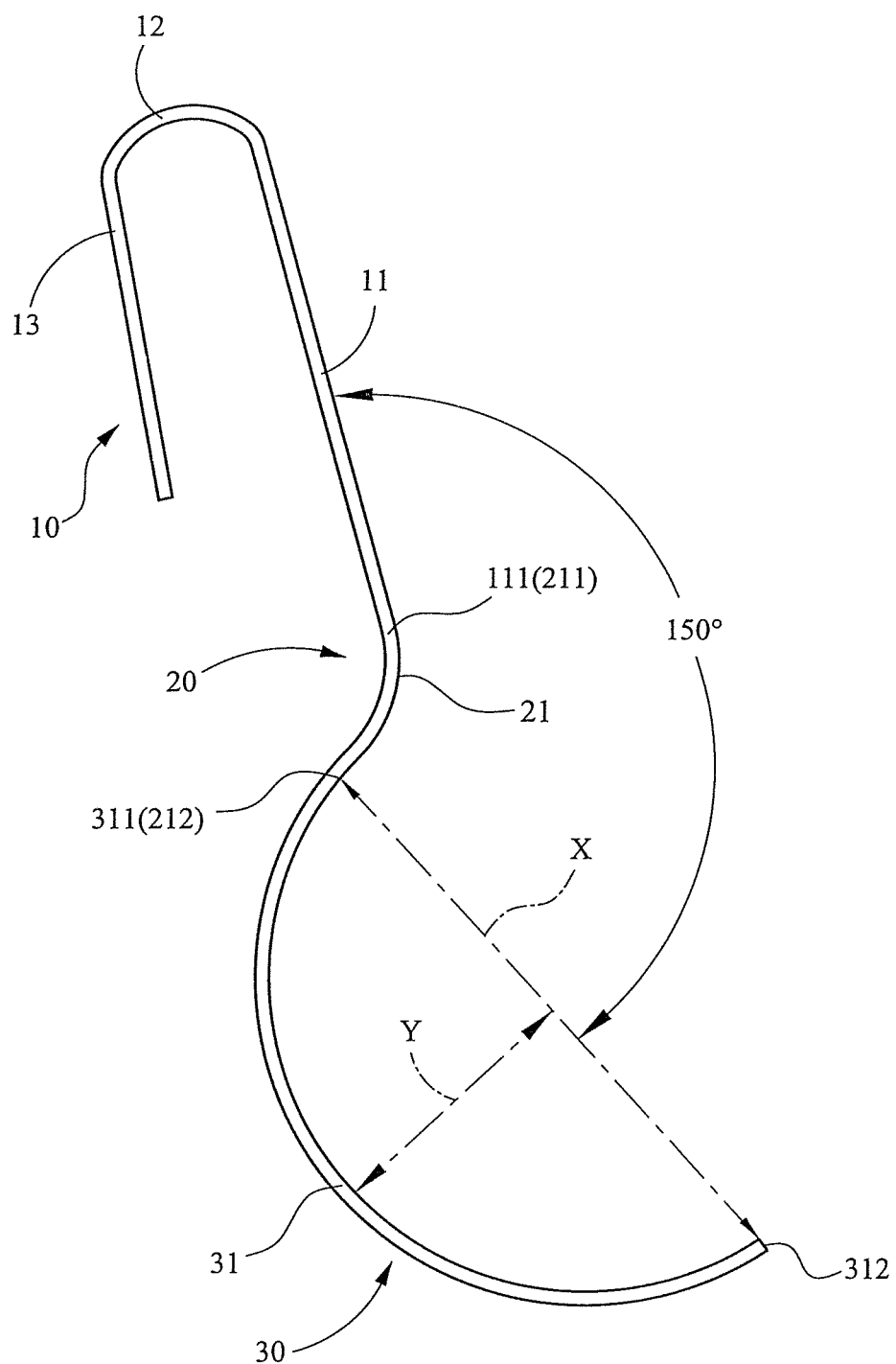
FIG. 3C is a side elevation view of a third aspect of the same illustrating the tongue anteriorizer made in a predetermined shape of 150-degree.
Figure 3D:
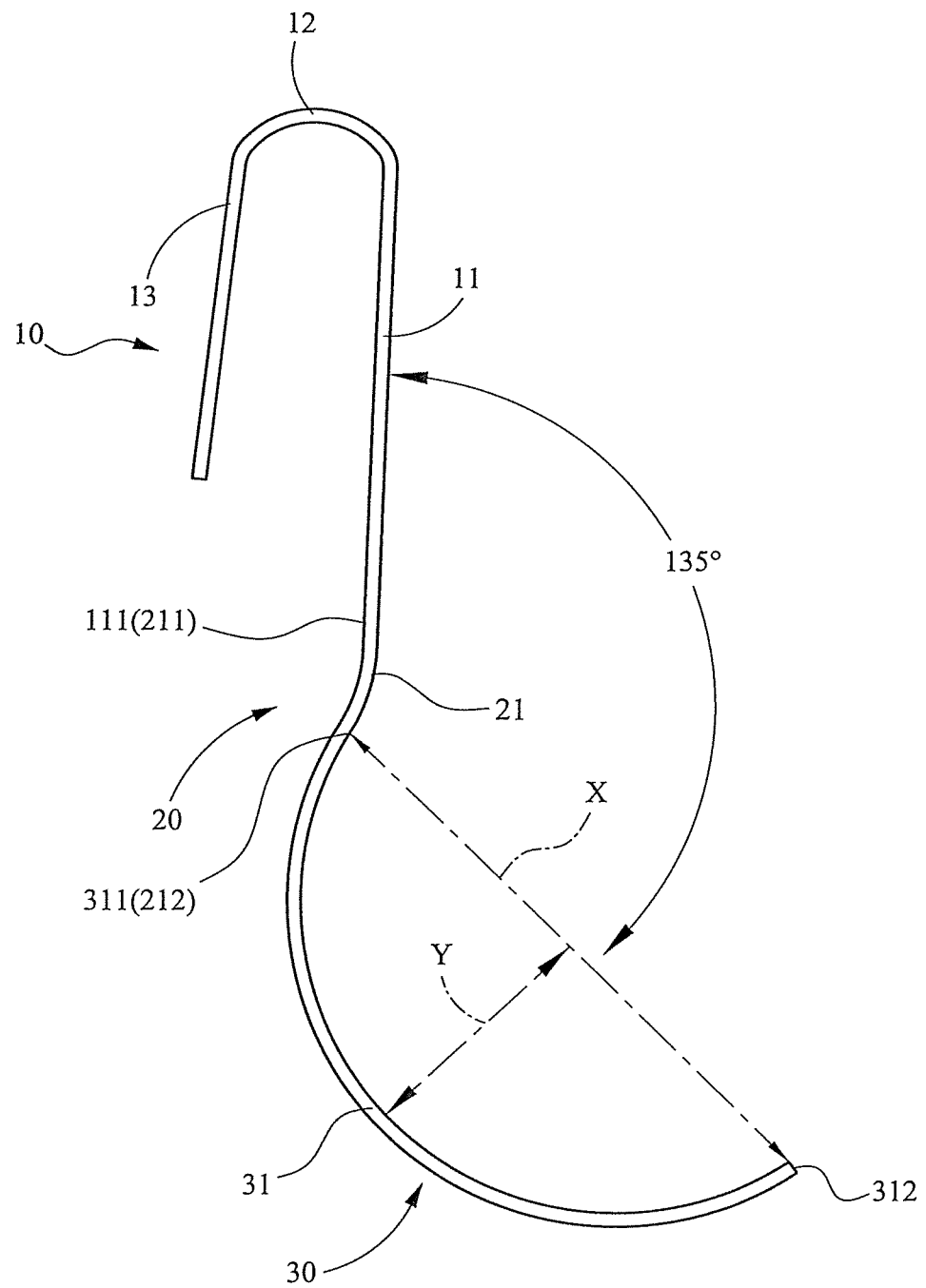
FIG. 3D is a side elevation view of a fourth aspect of the same illustrating the tongue anteriorizer made in a predetermined shape of 135-degree.
Figure 3E:
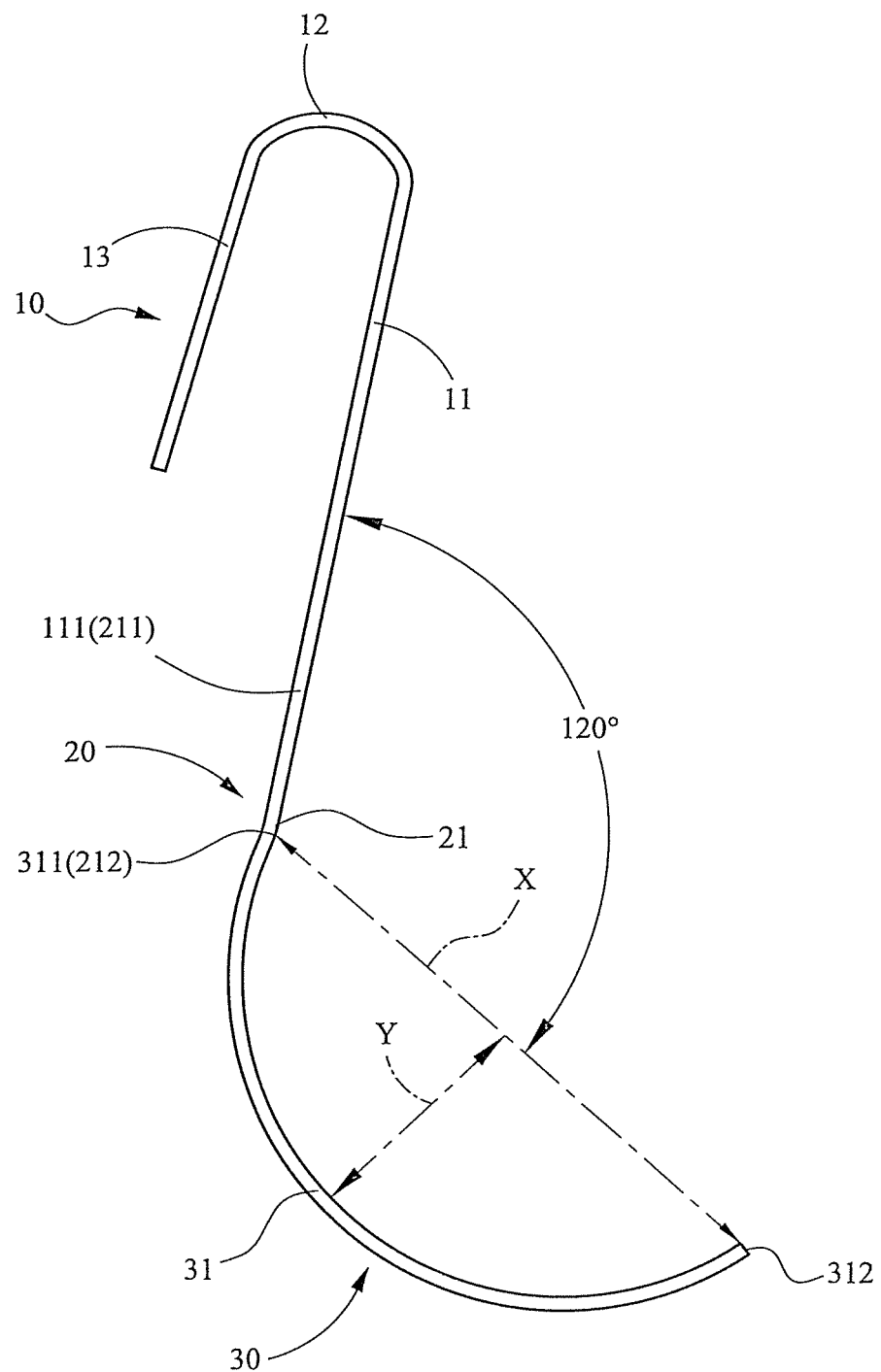
FIG. 3E is a side elevation view of a fifth aspect of the same illustrating the tongue anteriorizer made in a predetermined shape of 120-degree.
Figure 3F:
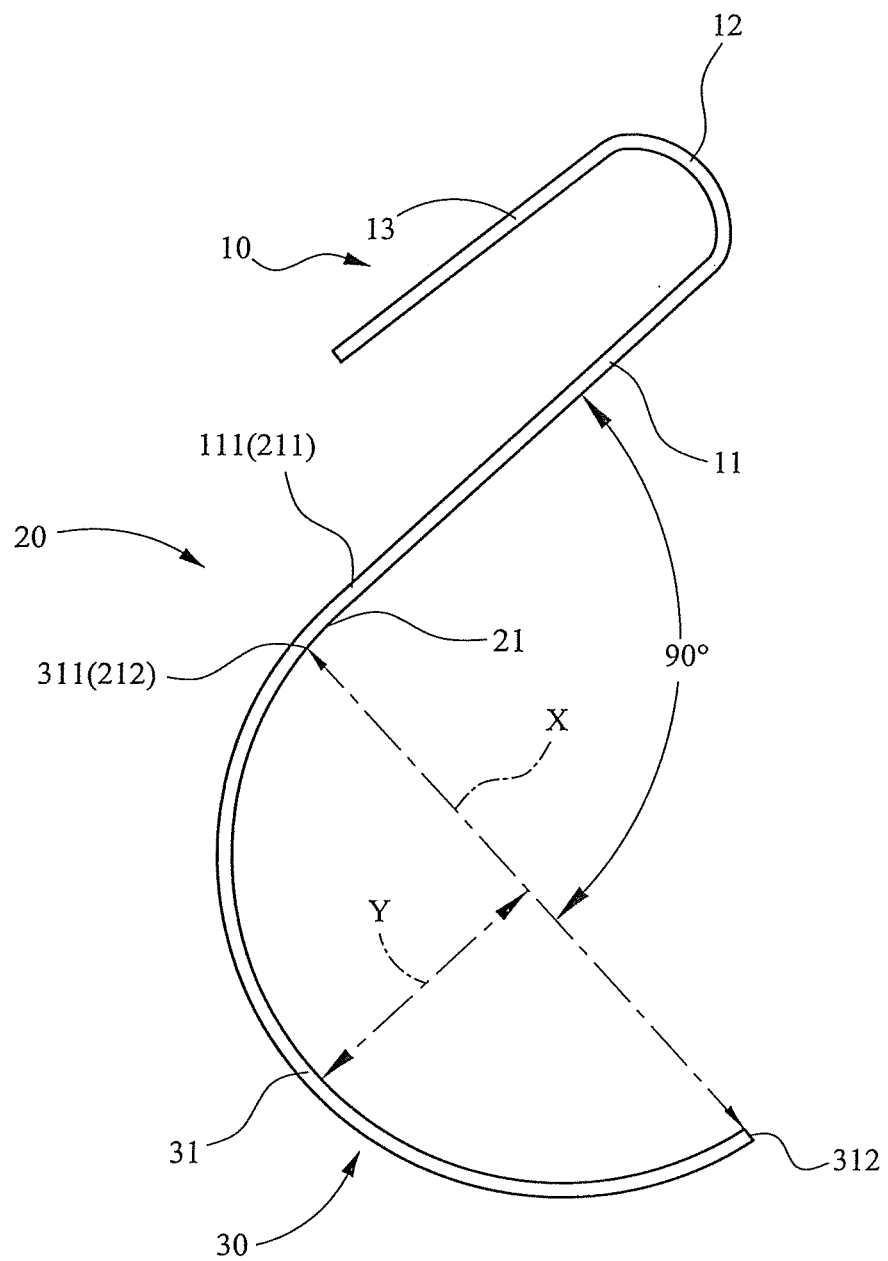
FIG. 3F is a side elevation view of a sixth aspect of the same illustrating the tongue anteriorizer made in a predetermined shape of 90-degree.
Figure 4A:
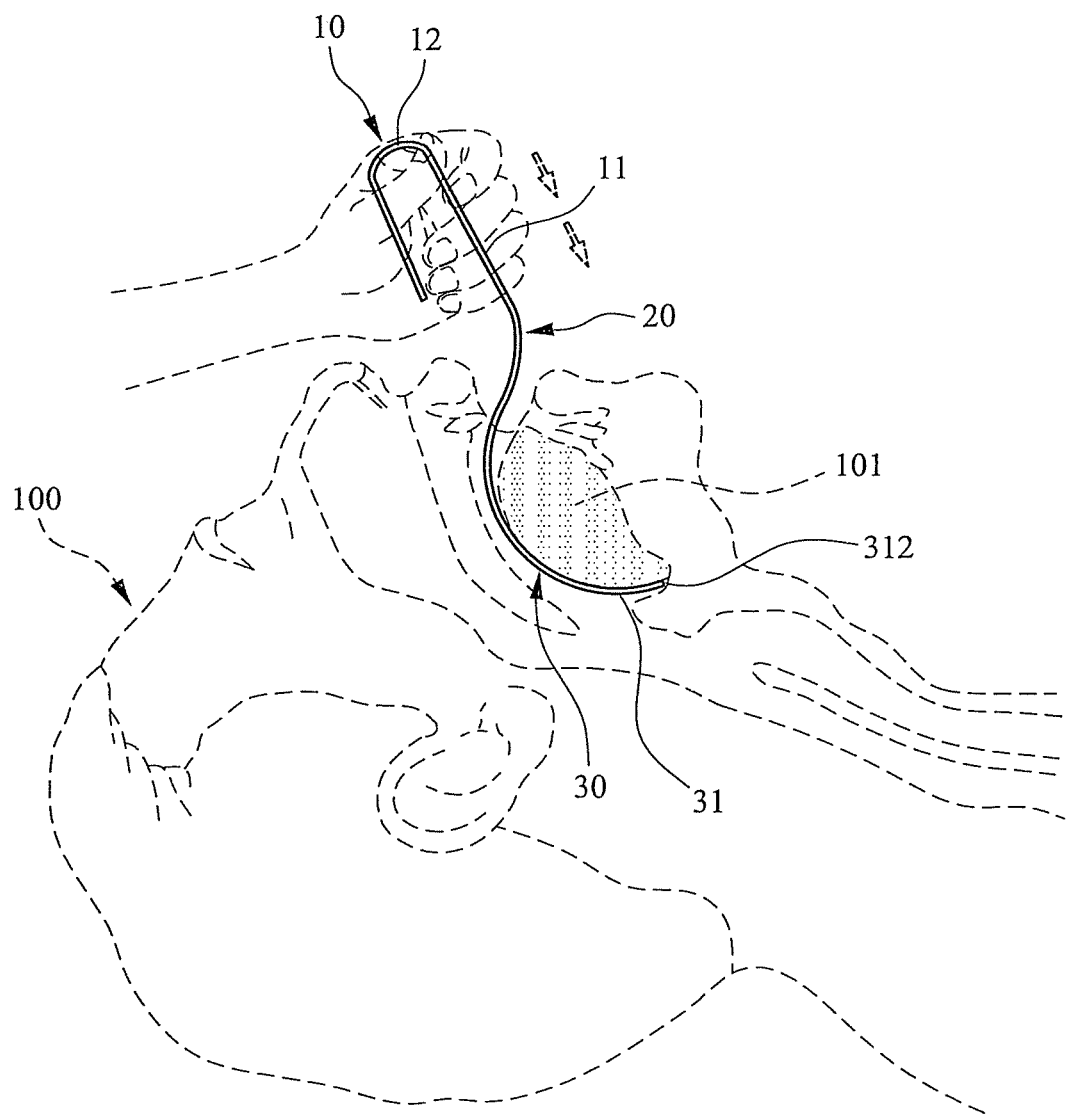
FIGS. 4A, 4B, 4C, 4D, and 4E are side views showing steps of inserting the tongue anteriorizer of FIG. 3A, into the base of the posterior part of the tongue of a patient, respectively.
Figure 4B:
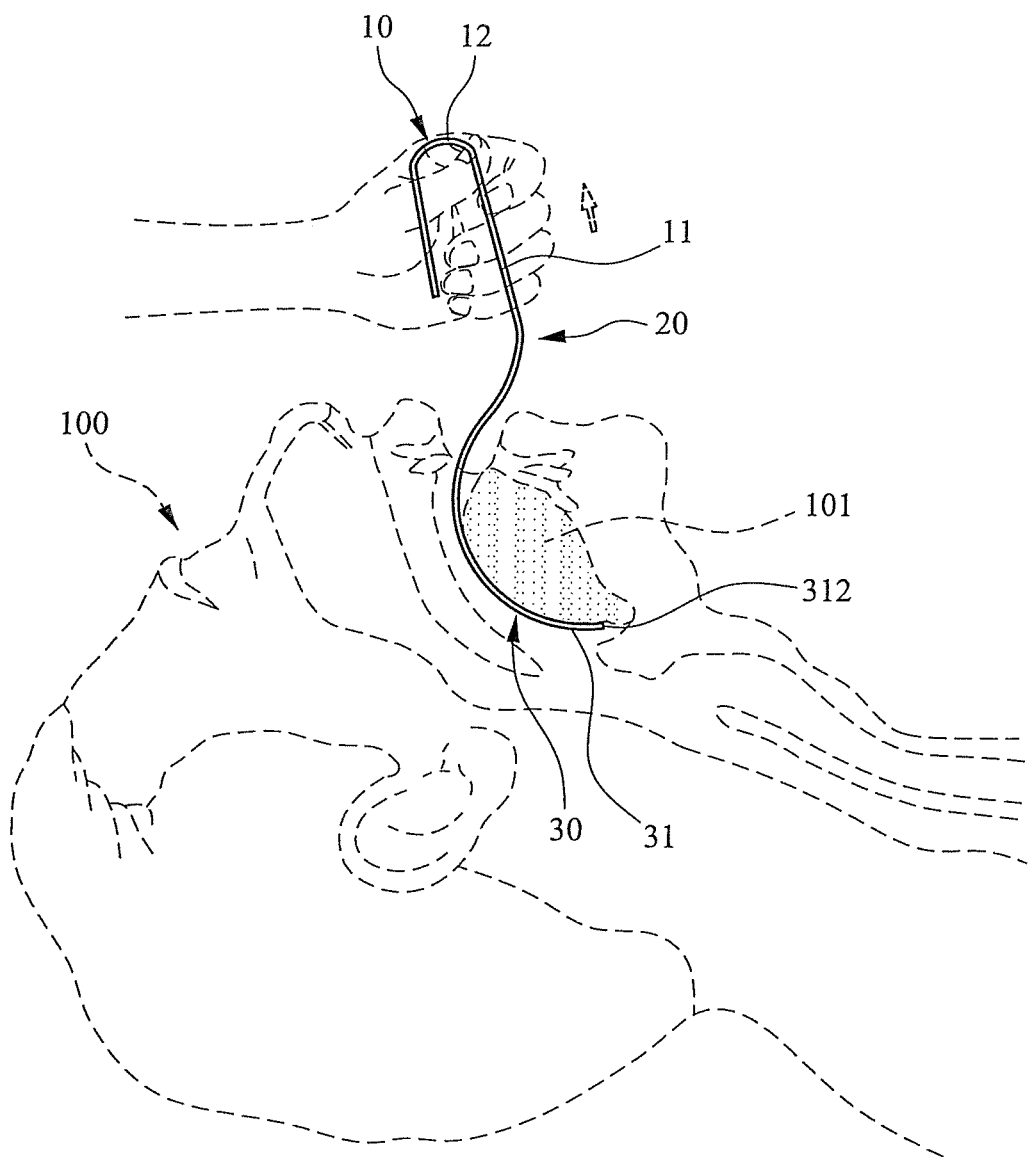
Figure 4C:
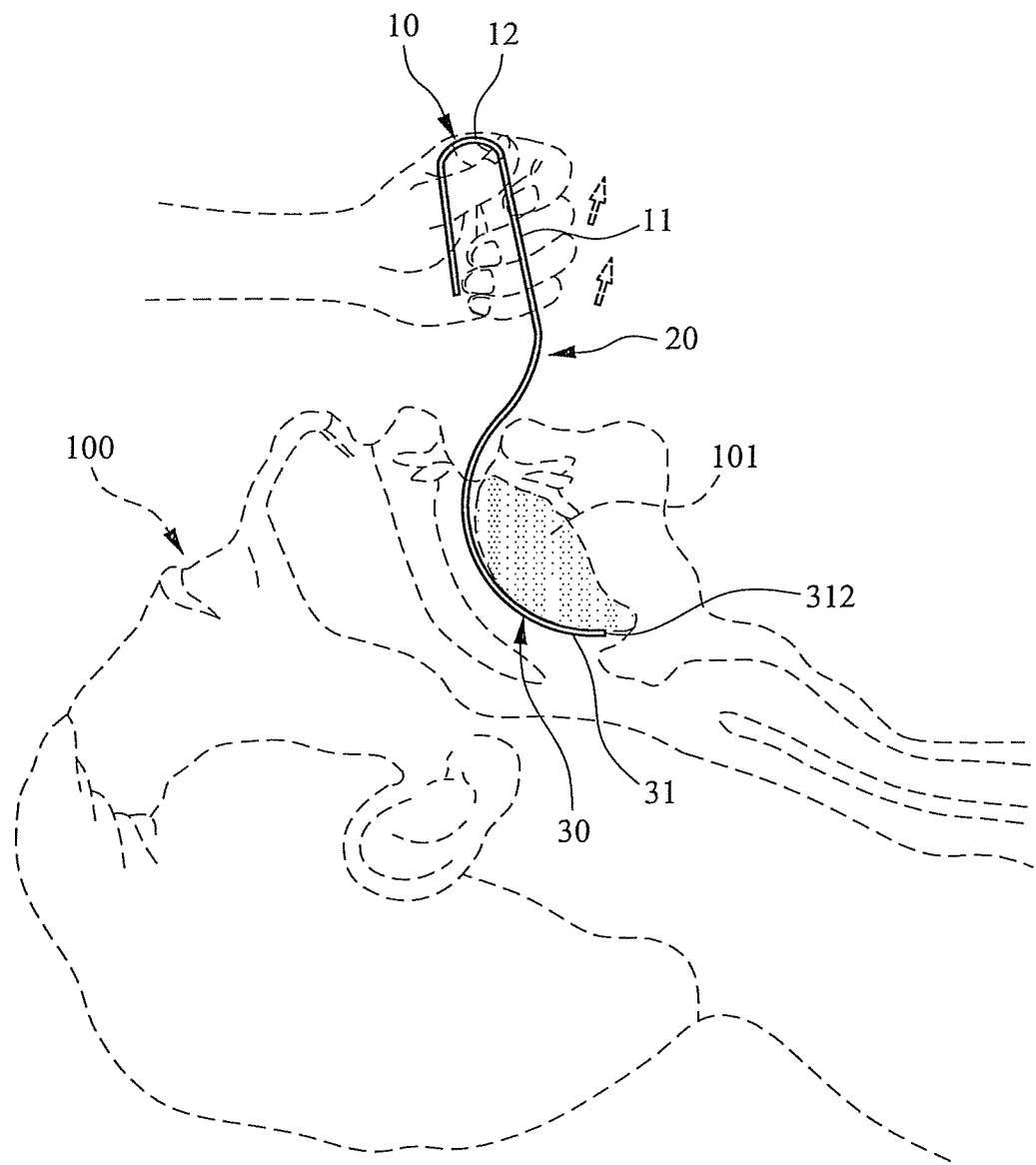
Figure 4D:
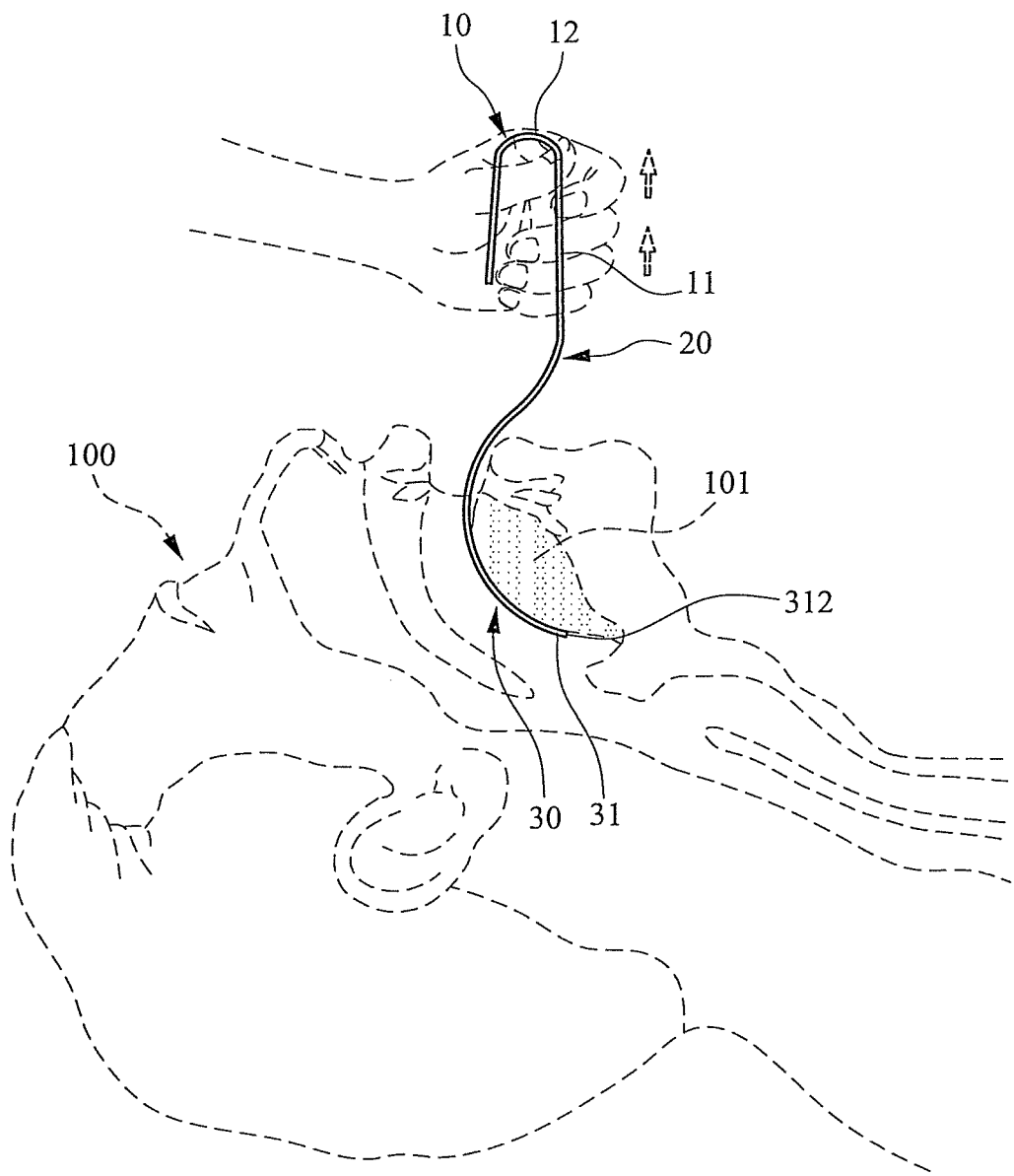
Figure 4E:
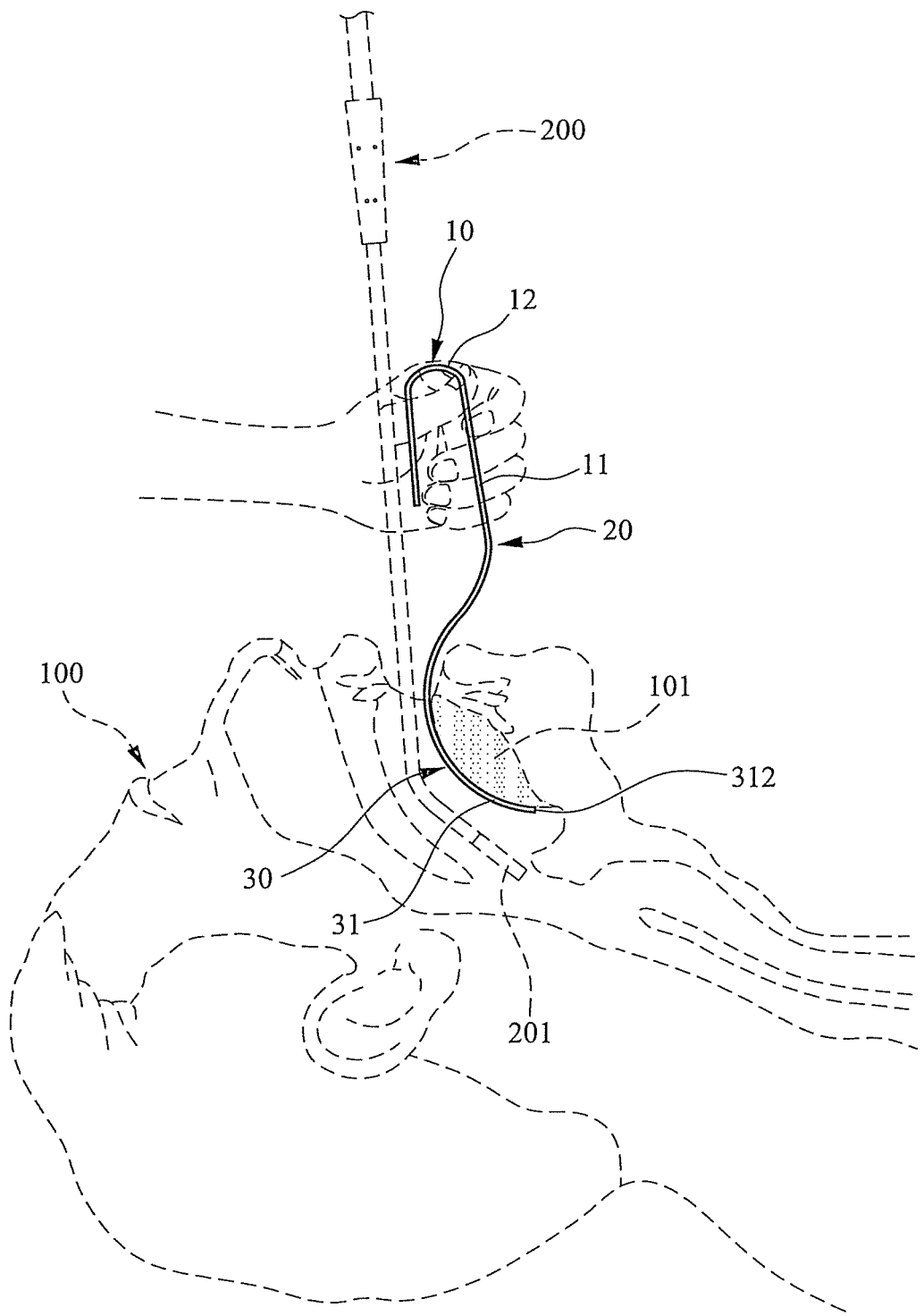
Figure 5:
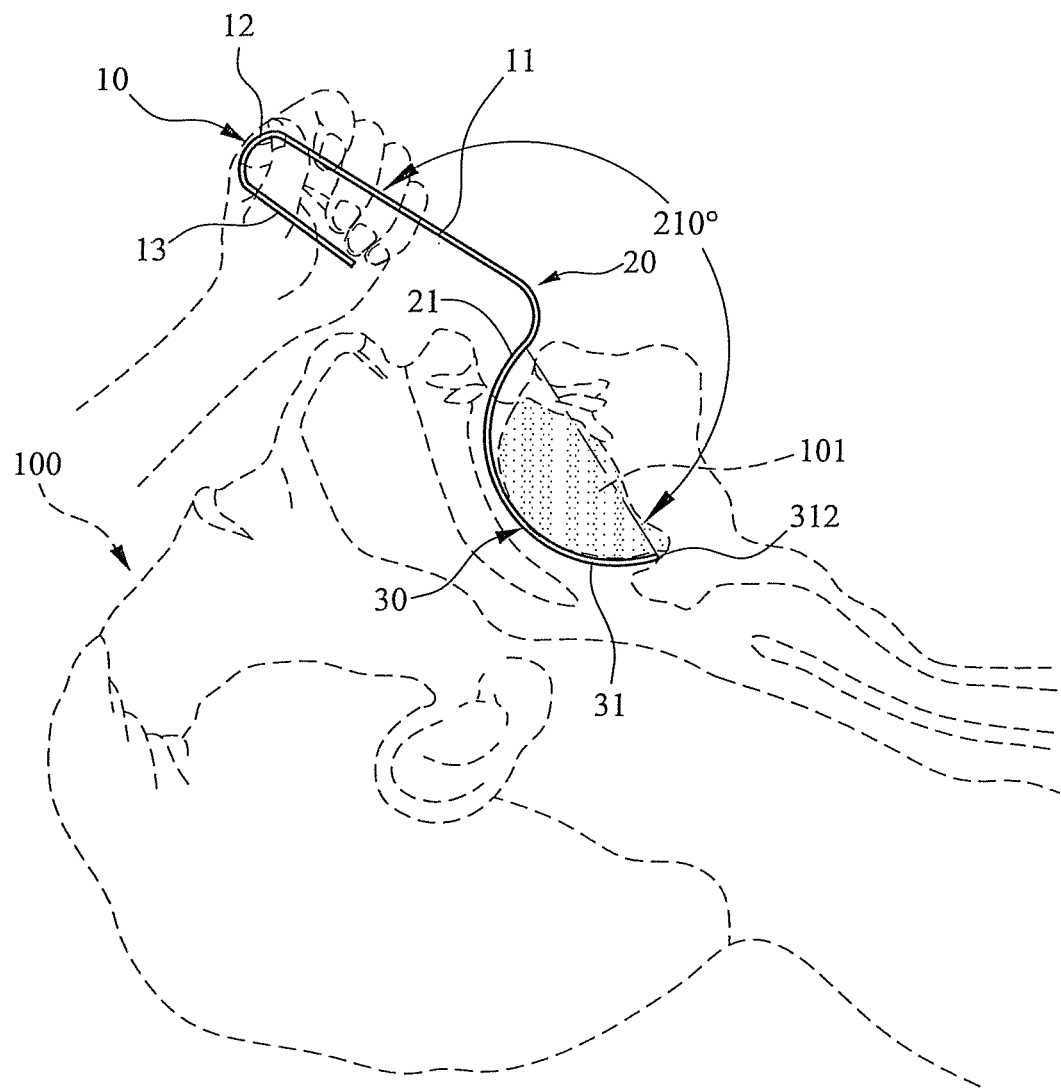
FIG. 5 is a side view showing of inserting the tongue anteriorizer of FIG. 3B into the oral part of a patient.
Figure 6:
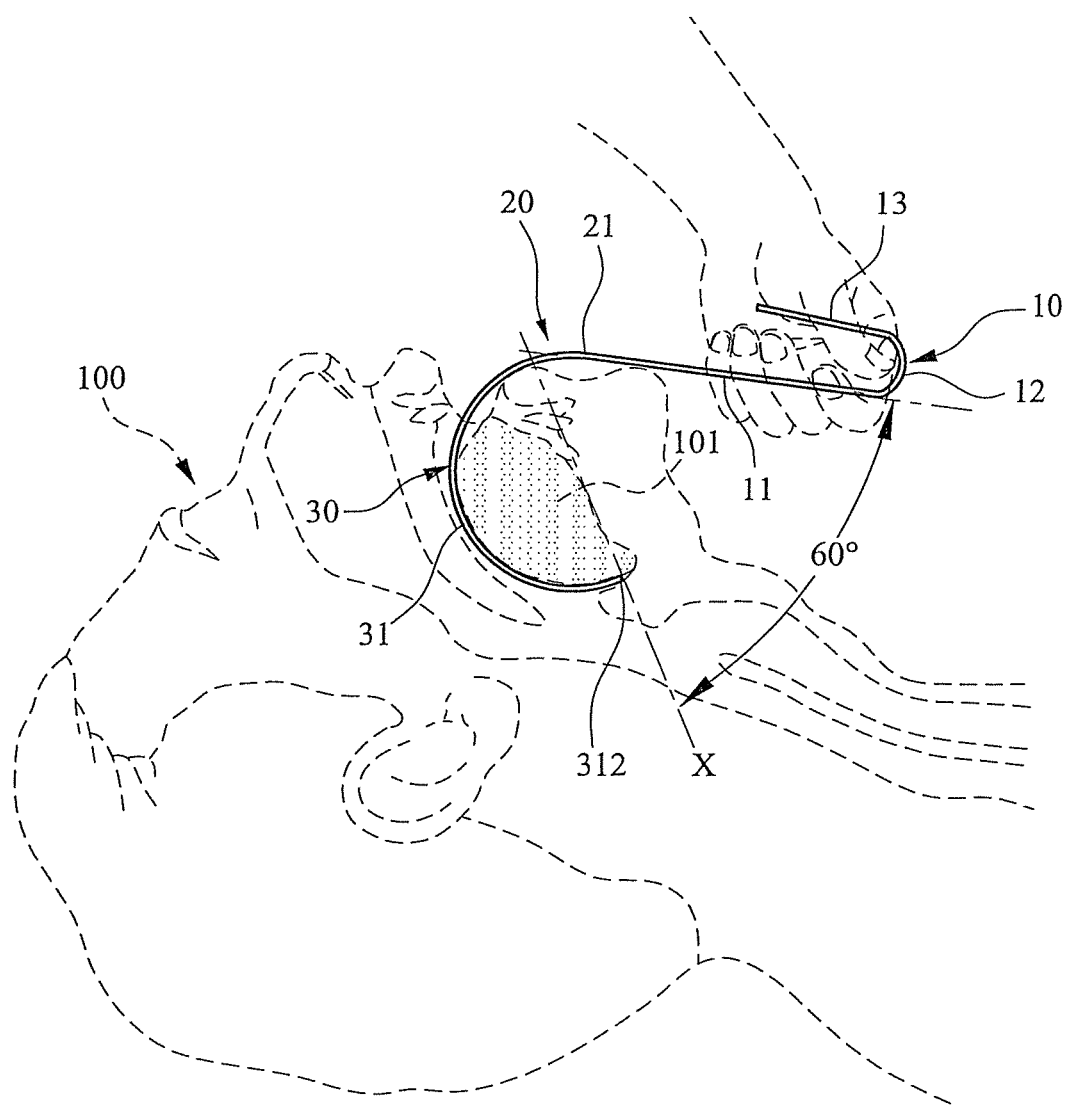
FIG. 6 is a side view similar to FIG. 5 showing the tongue anteriorizer in a shape of 60-degree.
Figure 7A:
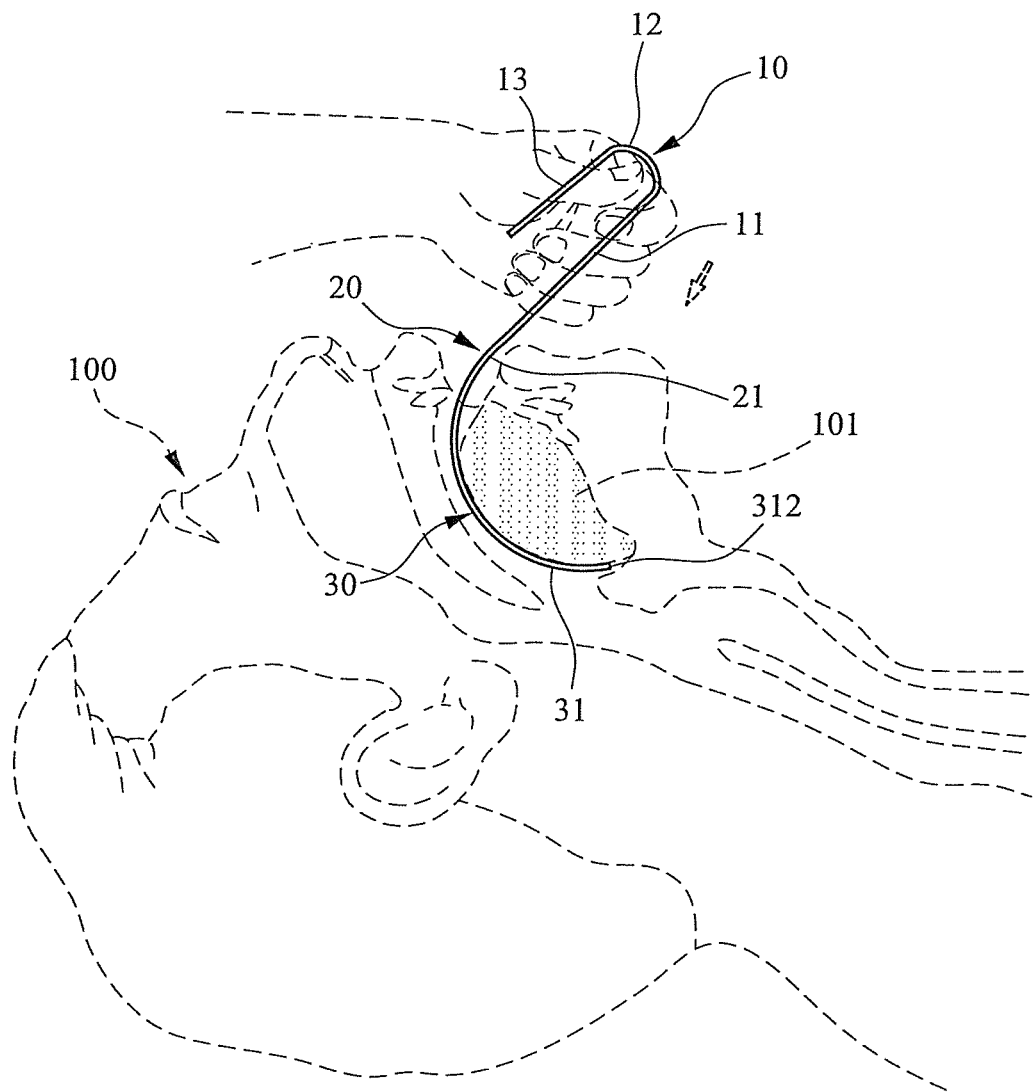
FIGS. 7A, 7B, and 7C are side views showing steps of inserting the tongue anteriorizer of FIG. 3F into the base of the posterior part of the tongue of a patient respectively.
Figure 7B:
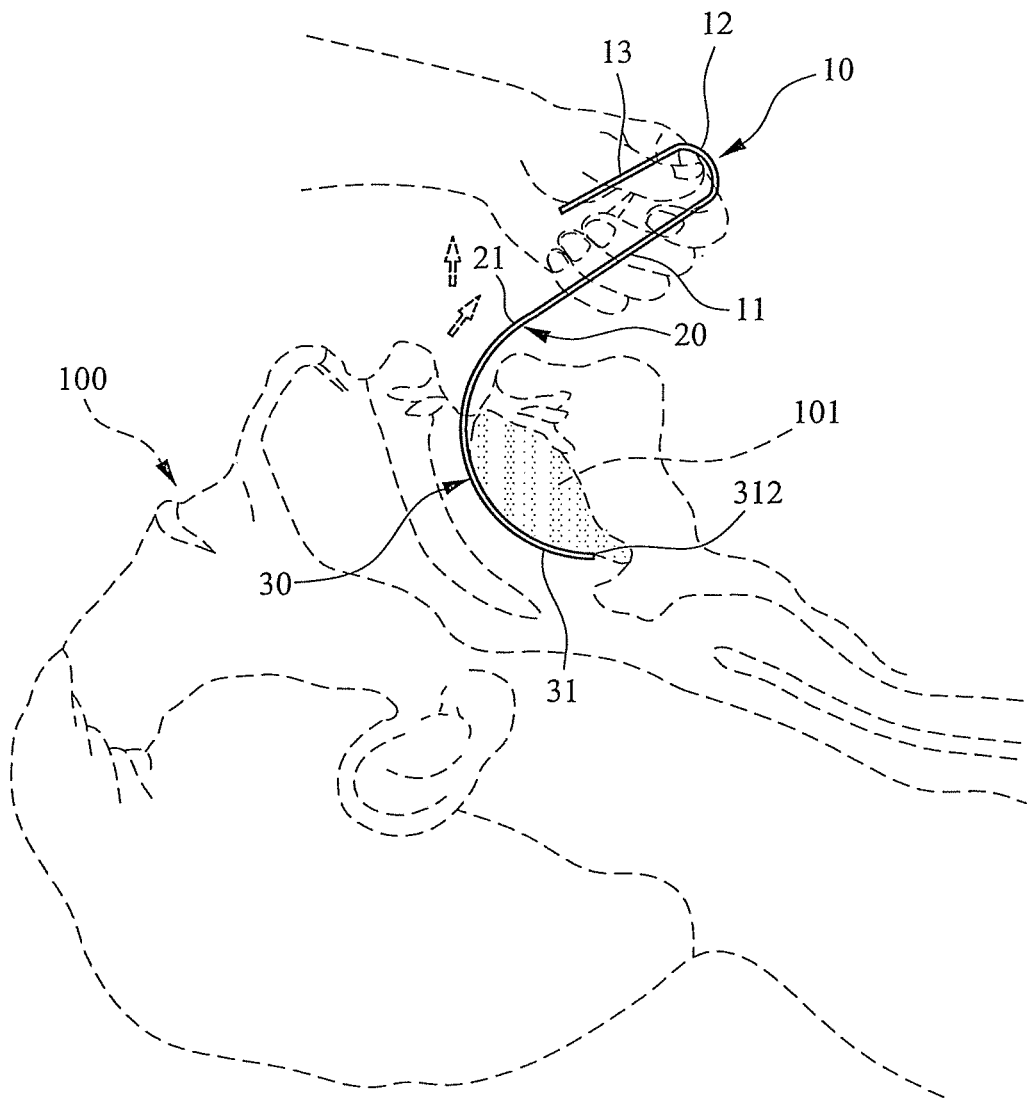
Figure 7C:
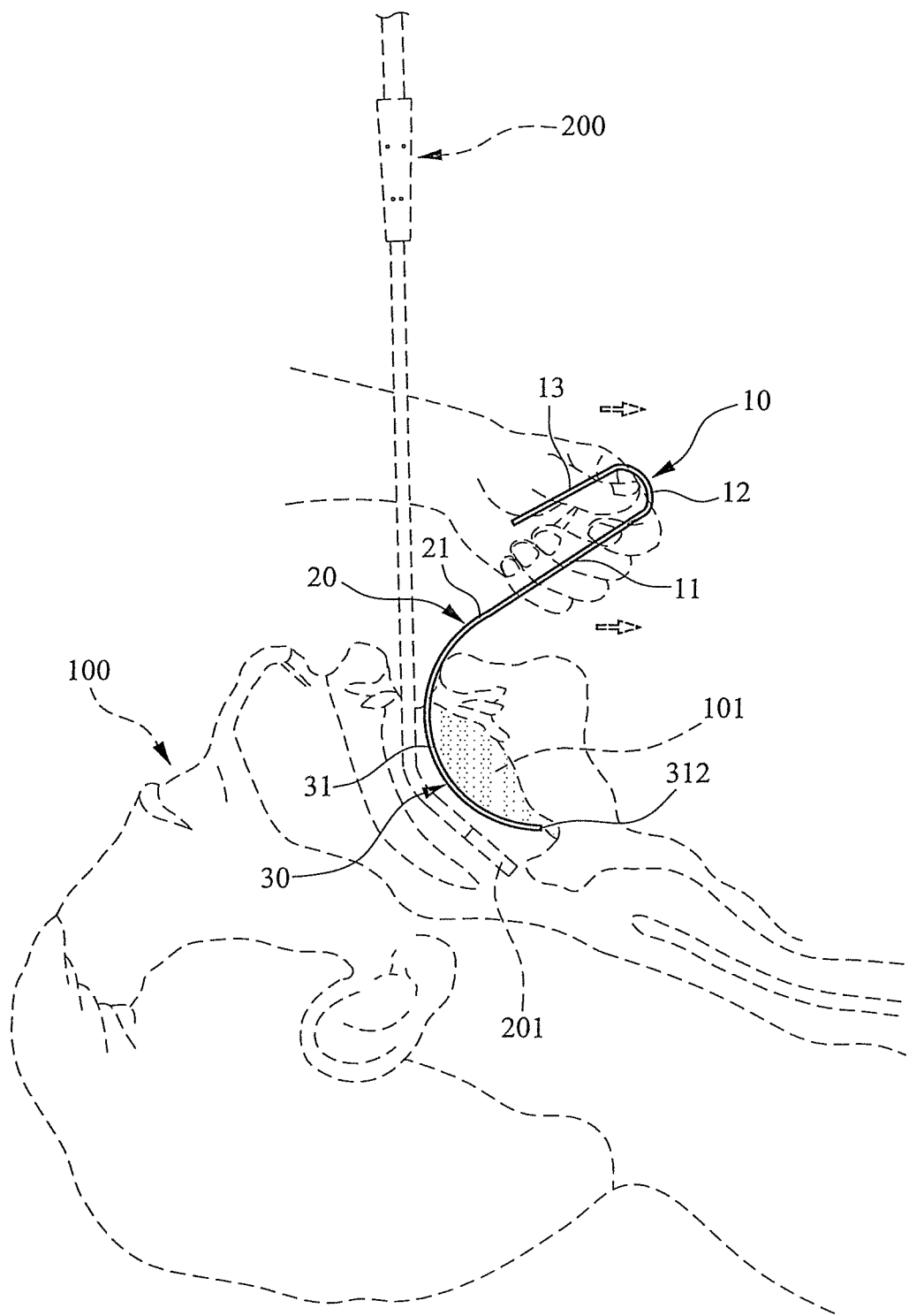

The handle 10 includes a main portion 11, an extension 13 substantially parallel to the main portion 11, and a bent interconnection 12 interconnecting the main portion 11 and the extension 13. In actual use, the length of the main portion 11 of the handle 10 is approximately the length of the palm of user's hand held. The connecting part 20 includes a curved connecting member 21 having an end 211 formed with a handle end 111 of the main portion 11, and the other end 212 formed with a curved portion 31 of the tongue lifting part 30. It is understood that the curved portion 31 of the tongue lifting part 30 is made from a plate-like strip having a uniform thickness. The curved portion 31 of the tongue lifting part 30 has a first end 311 and a second end 312, and the second end 312 is open. As viewed from the FIG. 2, the first end 311 (212) is a conversion point of two curves of the curved portion 31 and the curved connecting member 21. It is also to be understood that the point of the first end 311 (212) is substantially existed in all the figures. Further, the curved portion 31 has a width defined by two substantially parallel edges 316 (see FIG. 1).

It is noted that the handle 10 may be shaped differently from the shown one in other embodiments. It is further noted that in addition to the connecting member 21 of the connecting part 20 can be shaped as a curved shape as shown in FIGS. 3A to 3E, it can also be shaped as a straight part (see FIG. 3F). Alternatively, the connecting member 21 can be shaped other than a curve or a straight line in other embodiments depending on actual requirement. The tongue lifting part 30 can be made from a long strip of flat material by bending it into a predetermined shape, i.e. bending only along the long dimension 310 (see FIG. 2). Furthermore, it is noted that the curved portion 31 is made from a long dimension 310 and a short dimension 316, wherein the long dimension 310 is curved to form the curved portion 31 and the short dimension 316 is substantially straight, and wherein a subtense X is defined by joining the first end 311 and the second end 312 of the curved portion 31 and forms an angular relationship with the straight handle end 111 of the main portion 11, defining an angle ranged from 60 degrees to 210 degrees, respectively, as shown in FIGS. 3A-3F, and FIGS. 5, 6.

A maximum distance from the subtense X to the curved portion 31 is indicated by a dotted line is a depth Y. It will be noted that the curved portion 31 of the tongue lifting part 30 is an arc of a circle or an arc of an ellipse itself, the length of the curved portion 31 is smaller than that of the semicircle or than that of the semi-ellipse itself. It means that the length of the subtense X is smaller than that of radius of circle or than that of major axis of the ellipse.

Preferably, the ratio of the length of the depth Y to that of the subtense X is in the range from ¼ to ½, for example, the length of the subtense X used for an infant, a children and an adult are about 5-7 cm, 7-9 cm and 9-13 cm respectively.

As shown in FIGS. 3A to 3E and 4A to 4E, the connecting part 20 is curved, the connecting member 21 is configured to made in a predetermined angle, and the tongue anteriorizer may be configured to shape in any other desired angle corresponding to the subtense X, respectively. Operation of the first configuration of the first preferred embodiment of the tongue anteriorizer of the invention is described in detail below. A medical employee may use one hand to hold the main portion 11 of the handle 10 and insert the curved portion 31 of the tongue lifting part 30 into the mouth of a patient 100 until the second end 312 reaches the base of the posterior part of the tongue 101 (see FIG. 4A). It is noted that the tongue 101 can be moved anteriorly. Further, the posterior part of the tongue 101 can be hooked by the second end 312 of the curved portion 31 prior to lifting the tongue 101 (see FIG. 4B). Next, the employee may pull the main portion 11 of the handle 10 in a direction out of the mouth to cause the curved portion 31 of the tongue lifting part 30 to exert force on the tongue 101 (see FIGS. 4C to 4D). Thus, the tongue 101 can be pulled by the curved portion 31 of the tongue lifting part 30 to move anteriorly along the top surface of the tongue 101. As a result, the laryngopharyngeal space is open and increased, thereby allowing an endoscope 200 to easily insert into the mouth and positioning an end 201 of the endoscope 200 at a correct position in a natural manner (see FIG. 4E).

It is understood that whether insertion of the endoscope or endotracheal intubation is success or not depending on moving the tongue anteriorly and lifting it correctly. The size and shape of the curved portion 31 of the tongue lifting part 30 have been carefully calculated after considering ergonomics and the natural moving of the muscles of the tongue 101. Therefore, the tongue anteriorizer of the invention is effective in the design and makes the device ergonomic.

Furthermore, as viewed from the FIGS. 4A-4E, and FIGS. 7A-7C, it is noted that the curvature portion 31 of the tongue lifting part 30 is substantially two parallel edges 316 with a uniform thickness. When it is inserted into the mouth until it reaches a base of a posterior part of the tongue and hooked then pulled the tongue out very convenient in accordance with the moving muscle natural trend of the tongue without having any feeling hurt for the patient. The feature of the tongue lifting part 30 in the design might make the device ergonomic.

Referring to FIGS. 3F, 6 and 7A to 7C, a second configuration of the first preferred embodiment of the tongue anteriorizer of the invention is shown. In this configuration of the first preferred embodiment, the connecting member 21 is made from a straight part, it means that in this configuration, the straight part of connecting member 21 is directly connected to the main portion 11 of the handle 10, and the first end 311 of the curved portion 31 is directly connected to the connecting member 21, such that the curved portion 31 is substantially equivalent to have a first end 311 directly connected to the main portion 11 of the handle 10 and an opposing second end 312 is open. As viewed from the FIG. 3F, the first end 311 (212) is a conversion point of the curved portion 31 and the straight part of connecting member 21. The straight part of the connecting member 21 can also be configured to provide a predetermined angle relationship with the subtense X, respectively as mentioned above. Operation of the second configuration of the first preferred embodiment of the tongue anteriorizer of the invention is substantially the same as that of the first configuration described above. Thus, a detailed description thereof is omitted for the sake of brevity.

Figure 8:
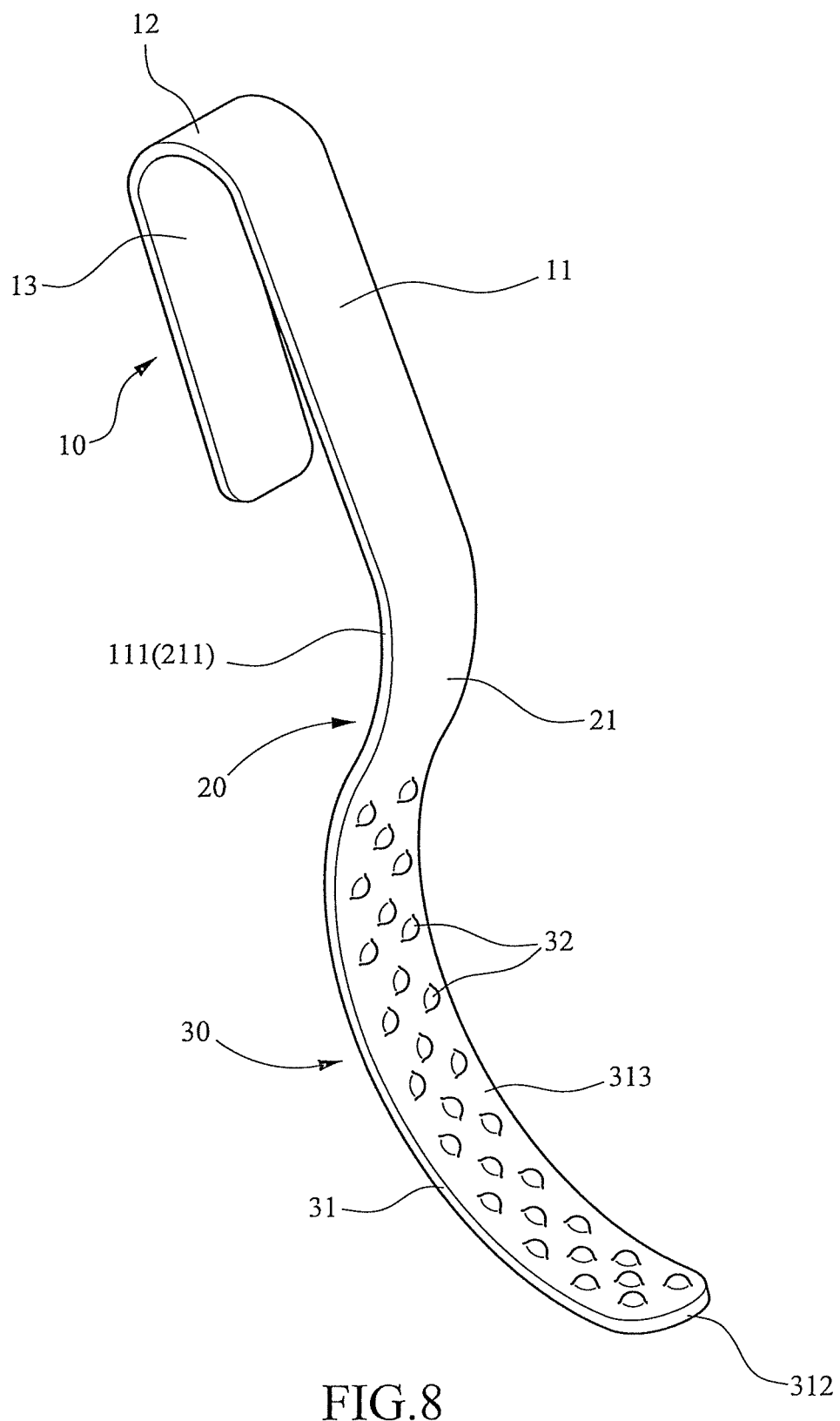
FIG. 8 is a perspective view of a tongue anteriorizer according to a second preferred embodiment of the invention.

Referring to FIG. 8, a tongue anteriorizer in accordance with a second preferred embodiment of the invention is shown. The characteristics of the second preferred embodiment are substantially the same as that of the first preferred embodiment except the following: A plurality of protrusions 32 are formed on a long strip surface 313 of the curved portion 31 of the tongue lifting part 30. The provision of the protrusions 32 can prevent the tongue lifting part 30 from slipping relative to the tongue.

Figure 9:
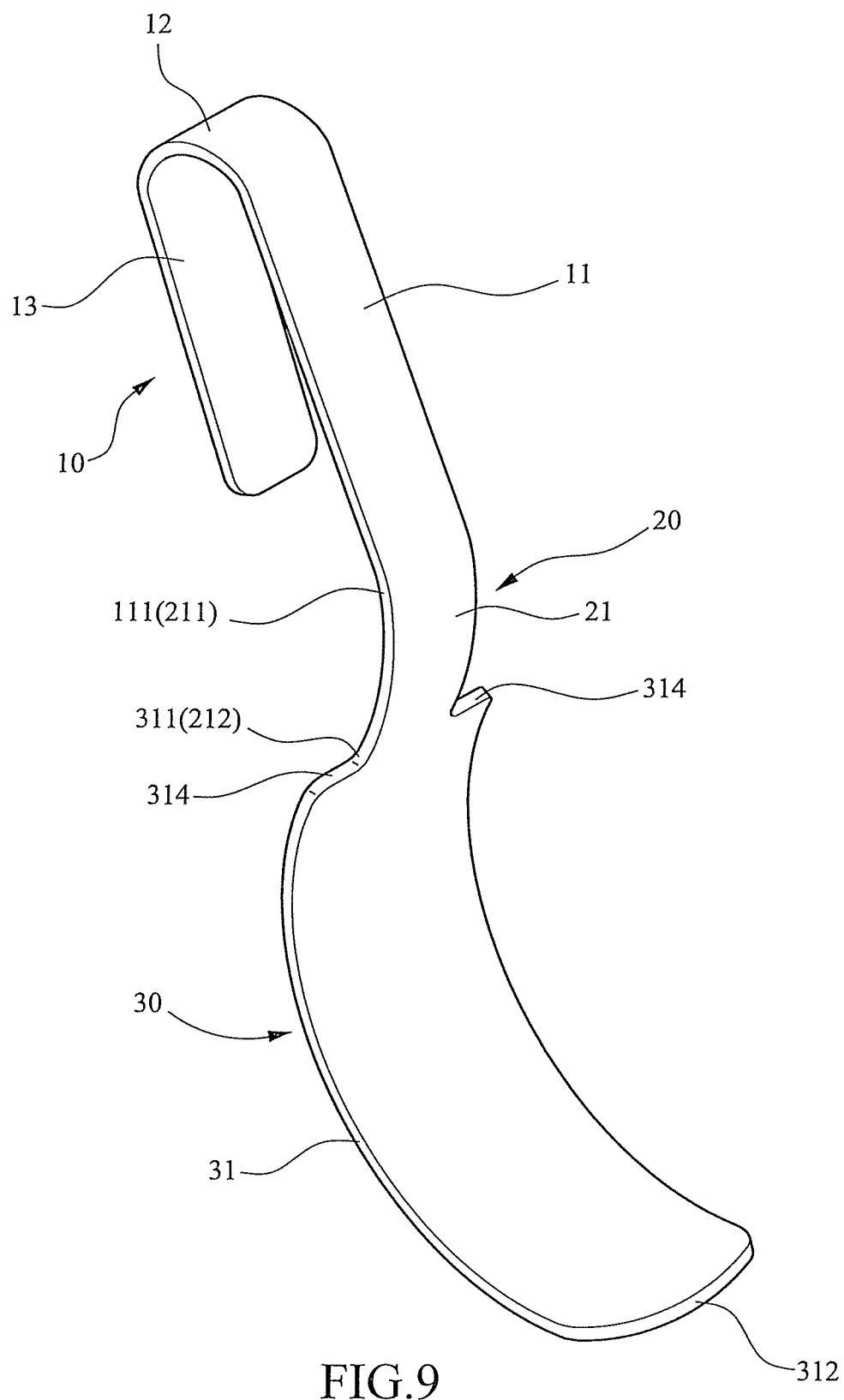
FIG. 9 is a perspective view of a first configuration of a tongue anteriorizer according to a third preferred embodiment of the invention.
Figure 10:
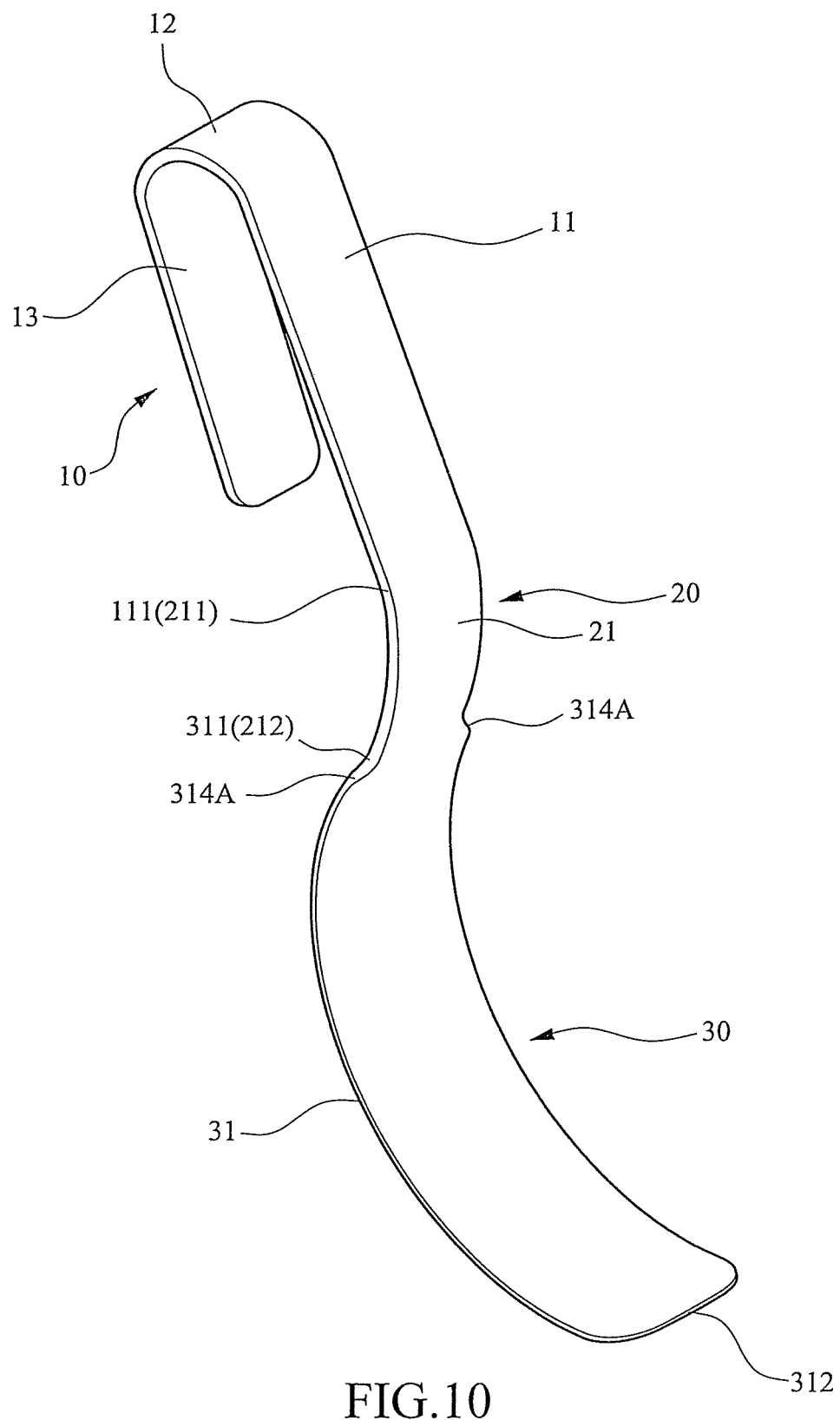
FIG. 10 is a perspective view of the second configuration of the tongue anteriorizer according to the third preferred embodiment of the invention.

Referring to FIGS. 9 and 10, a tongue anteriorizer in accordance with a third preferred embodiment of the invention is shown. The characteristics of the third preferred embodiment are substantially the same as that of the first preferred embodiment except the following: In a first configuration, two opposite flat shoulders 314 are formed between the connecting member 21 of the connecting part 20 and the curved portion 31 of the tongue lifting part 30 so that width of the curved portion 31 of the tongue lifting part 30 is greater than that of the connecting member 21 of the connecting part 20, and the width of the curved portion 31 is less than twice that of the connecting part 20. In a second configuration, two opposite inclined shoulders 314A are formed between the connecting member 21 of the connecting part 20 and the curved portion 31 of the tongue lifting part 30 so that width of the curved portion 31 of the tongue lifting part 30 is greater than that of the connecting member 21 of the connecting part 20, and the width of the curved portion 31 is less than twice that of the connecting part 20.

Figure 11:
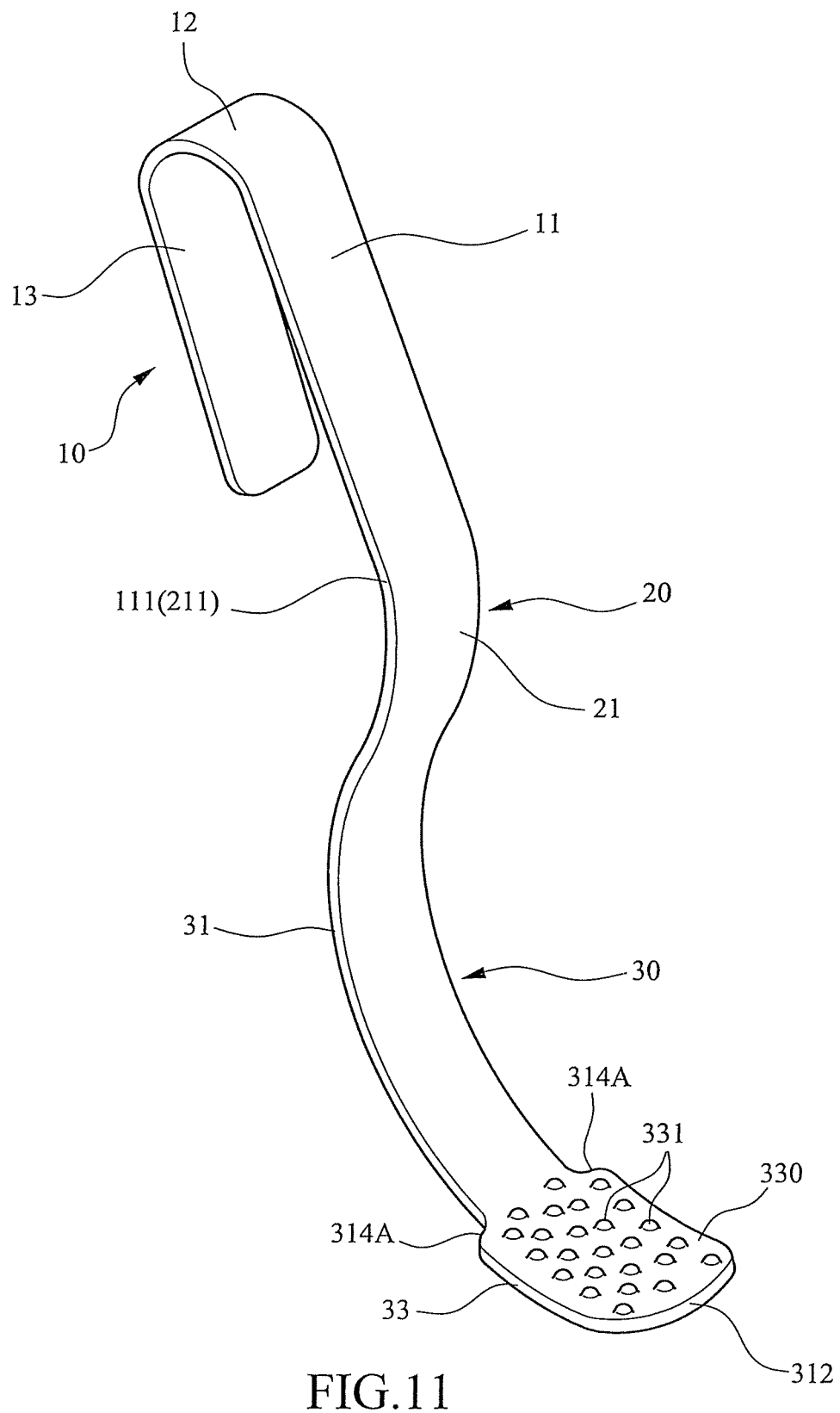
FIG. 11 is a perspective view of a tongue anteriorizer according to a fourth preferred embodiment of the invention.

Referring to FIG. 11, a tongue anteriorizer in accordance with a fourth preferred embodiment of the invention is shown. The characteristics of the fourth preferred embodiment are substantially the same as that of the first preferred embodiment except the following: A plurality of protrusions 331 are formed on a long strip surface 330 of an enlargement 33 of the curved portion 31 of the tongue lifting part 30 adjacent to the second end 312. Two opposite inclined shoulders 314A are formed between the enlargement 33 and the curved portion 31 of the tongue lifting part 30, and the width of the enlargement 33 is less than twice that of the connecting part 20.

Figure 12:
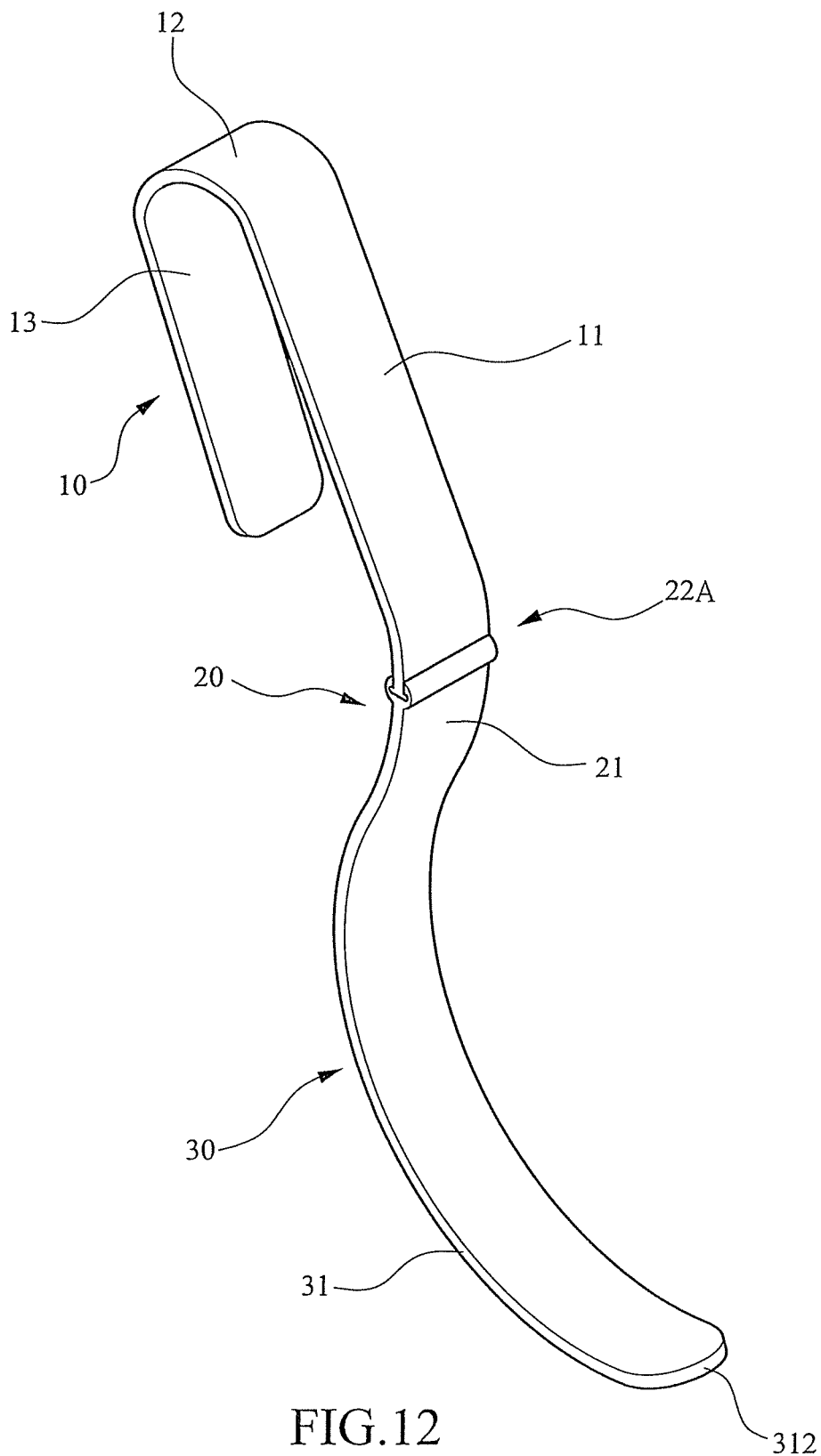
FIG. 12 is a perspective view of a tongue anteriorizer according to a fifth preferred embodiment of the invention.
Figure 13:
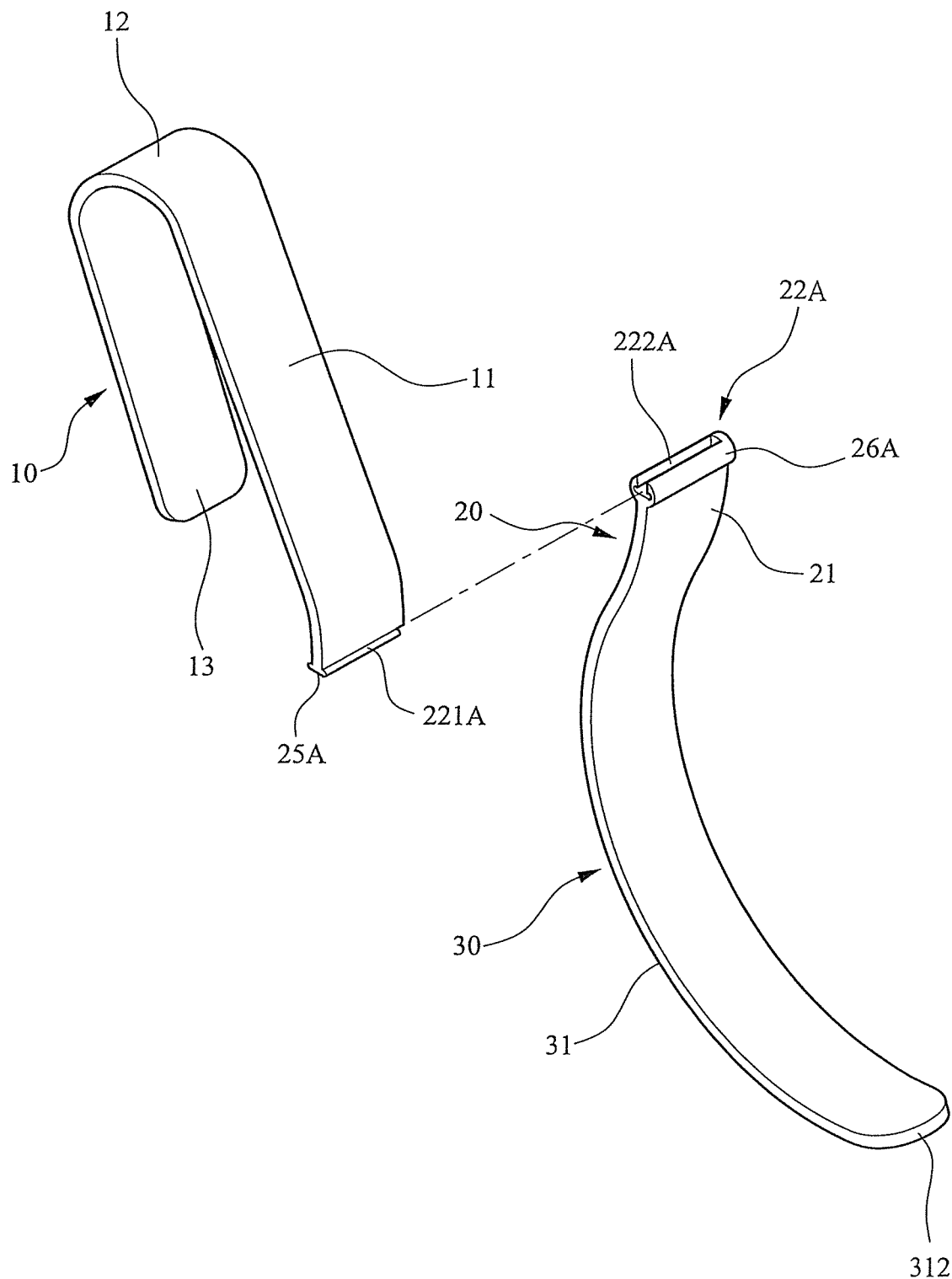
FIG. 13 is an exploded view of the tongue anteriorizer of FIG. 12.

Referring to FIGS. 12 and 13, a tongue anteriorizer in accordance with a fifth preferred embodiment of the invention is shown. The characteristics of the fifth preferred embodiment are substantially the same as that of the first preferred embodiment except the following: A joint 22A is formed on the connecting member 21 of the connecting part 20. The joint 22A includes a rail 25A formed with the main portion 11 of the handle 10 and having two opposite elongated projections 221A, and a groove member 26A formed with the curved portion 31 of the tongue lifting part 30 and having a groove 222A. The groove 222A is shaped complimentarily to the rail 25A so that the rail 25A can be slidably inserted into the groove 222A to fasten the handle 10 and the tongue lifting part 30 together. This is a two-piece embodiment of the tongue anteriorizer of the invention and it facilitates manufacturing, assembly, and transport.

Figure 14:
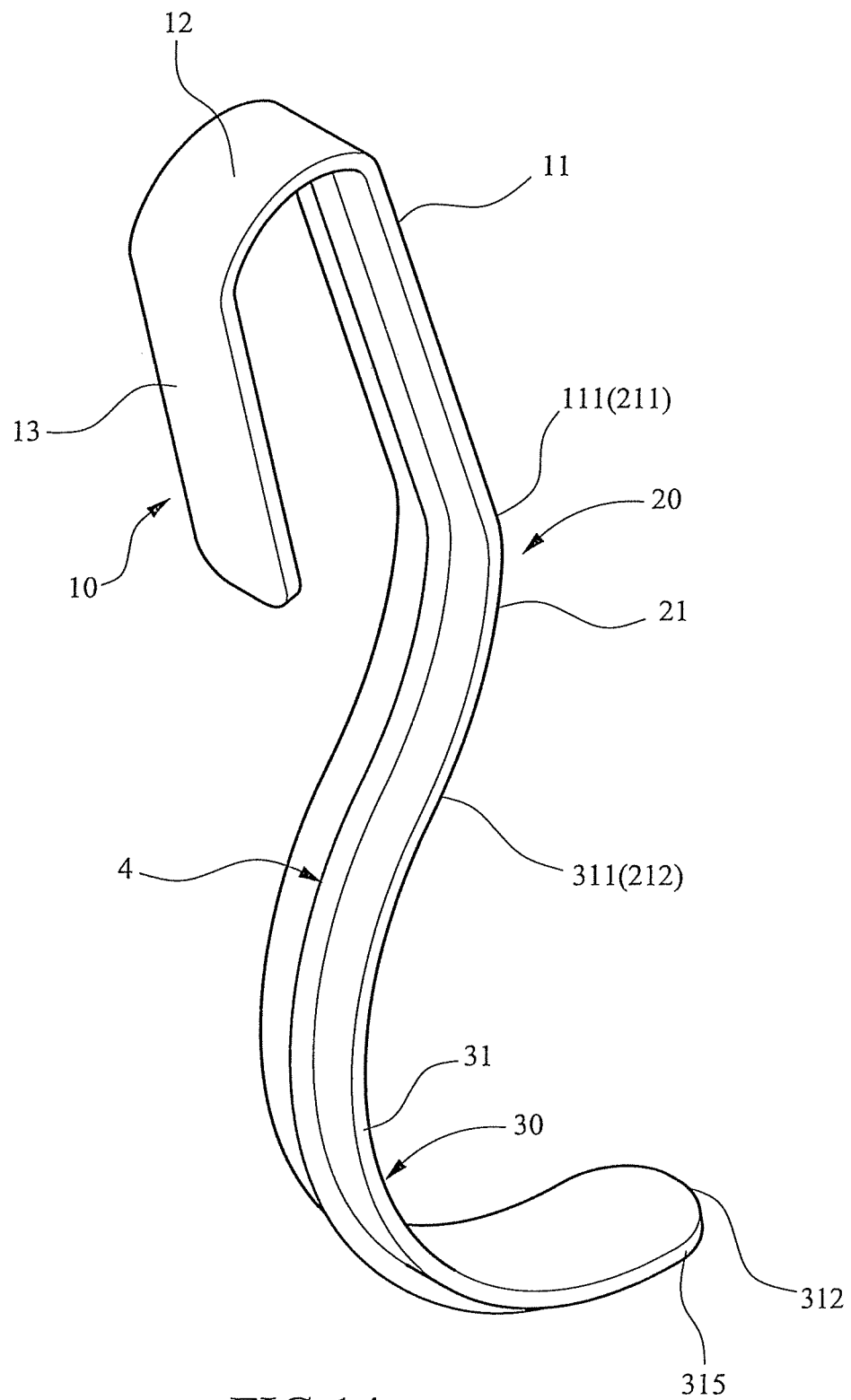
FIG. 14 is a perspective view of a tongue anteriorizer according to a sixth preferred embodiment of the invention.

Referring to FIG. 14, a tongue anteriorizer in accordance with a sixth preferred embodiment of the invention is shown. The characteristics of the sixth preferred embodiment are substantially the same as that of the first preferred embodiment except the following: A rib 4 is formed on the middle portion of the back of the tongue anteriorizer to increase the rigidity of the tongue anteriorizer.

Figure 15:
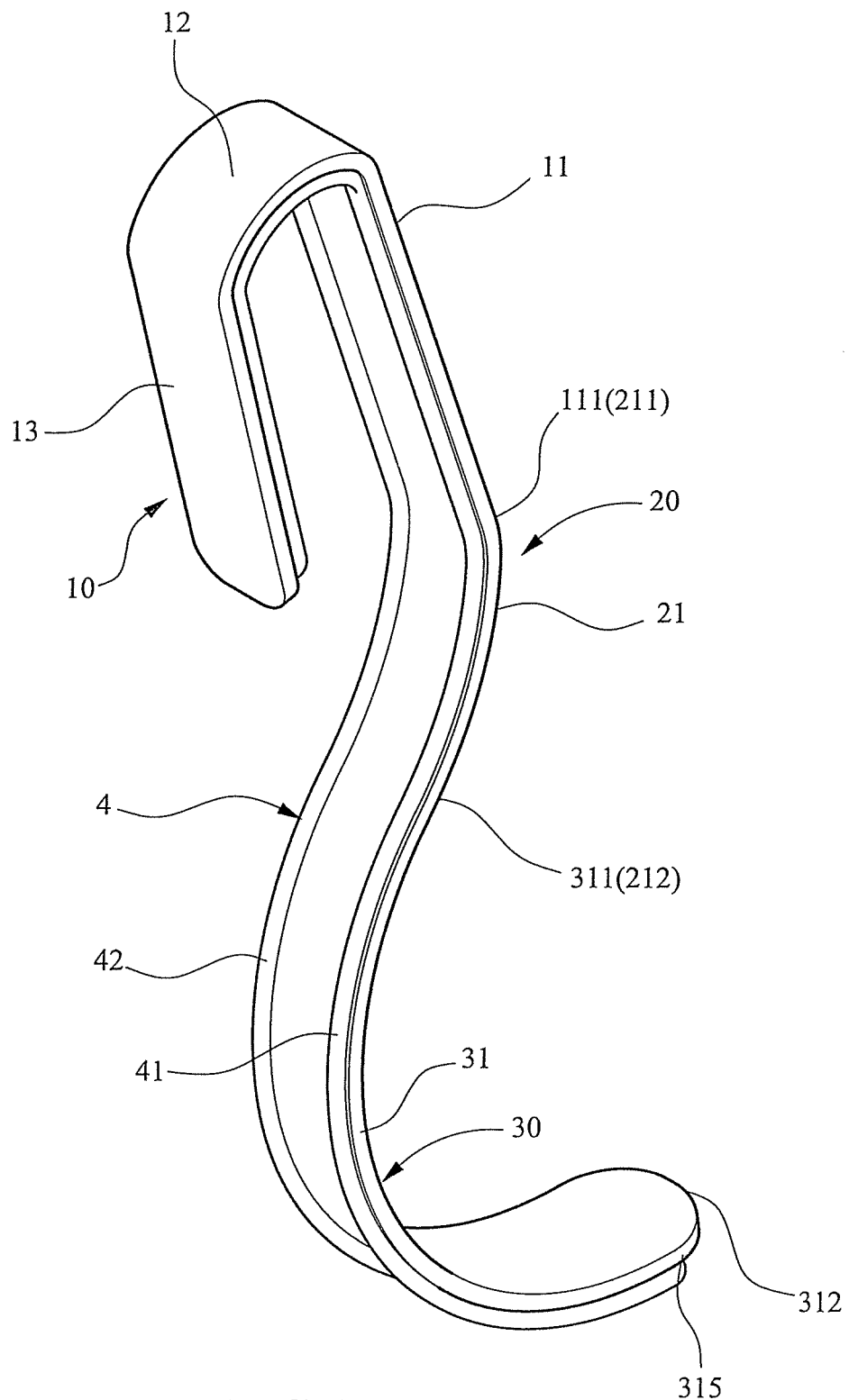
FIG. 15 is a perspective view of a tongue anteriorizer according to a seventh preferred embodiment of the invention.

Referring to FIG. 15, a tongue anteriorizer in accordance with a seventh preferred embodiment of the invention is shown. The characteristics of the seventh preferred embodiment are substantially the same as that of the first preferred embodiment except the following: Two ribs 41 and 42 are formed on both sides of the back of the tongue anteriorizer to increase the rigidity of the tongue anteriorizer.

Figure 16:
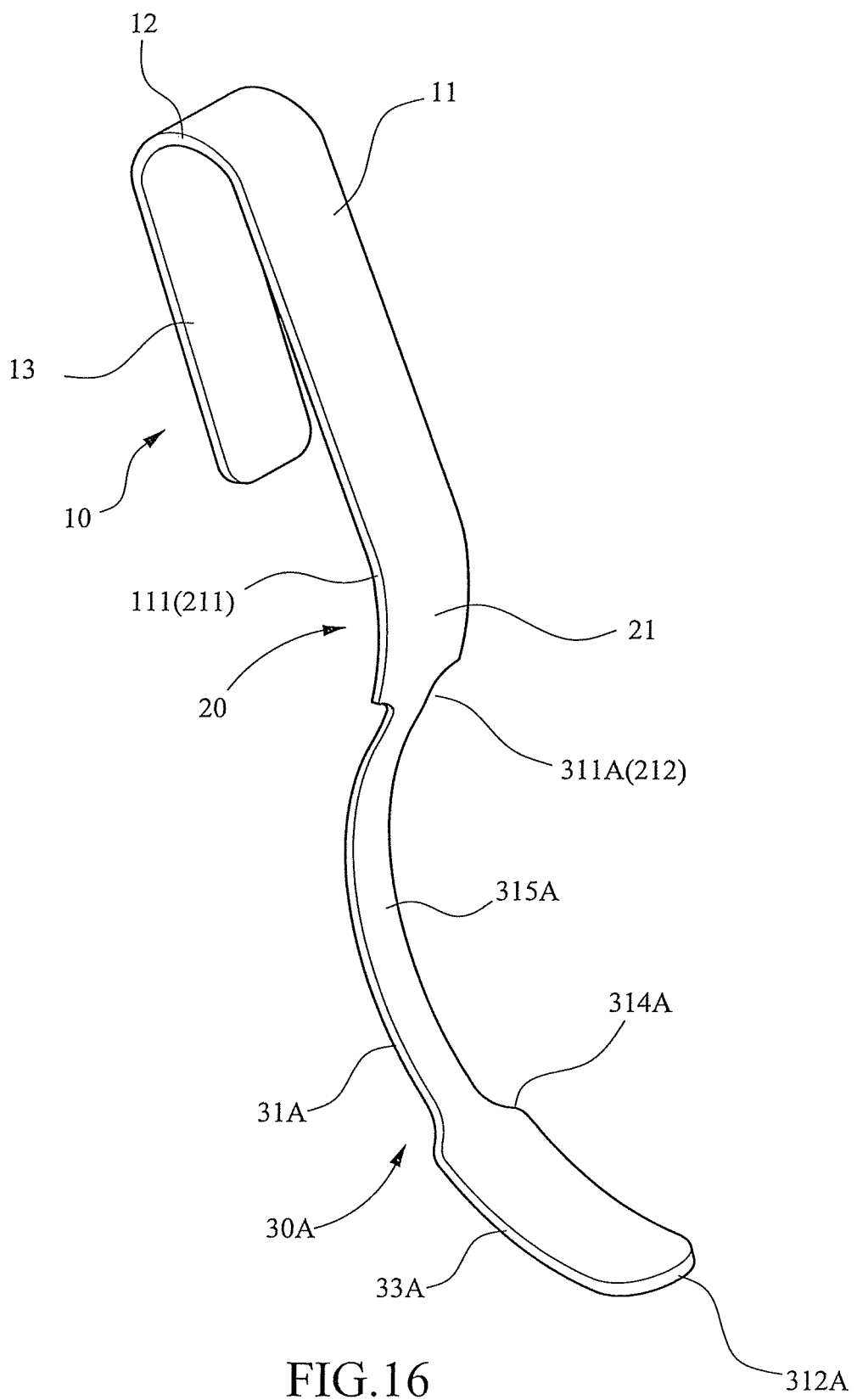
FIG. 16 is a perspective view of a tongue anteriorizer according to a eighth preferred embodiment of the invention.

Referring to FIG. 16, a tongue anteriorizer in accordance with a eighth preferred embodiment of the invention is shown. The characteristics of the eighth preferred embodiment are substantially the same as that of the first preferred embodiment except the following. The curved portion 31A of the tongue lifting part 30A are formed by a long strip narrower portion 315A and a long strip wider portion 33A adjacent to the narrower portion 315A. Two opposite inclined shoulders 314A are formed between the narrower portion 315A and the wider portion 33A of the curved portion 31A of the tongue lifting part 30A. It is noted that the optimum value of the slightly flexible deformation for both of the connecting part 20 and the tongue lifting part 30A has been carefully calculated after considering ergonomics.

Figure 17:
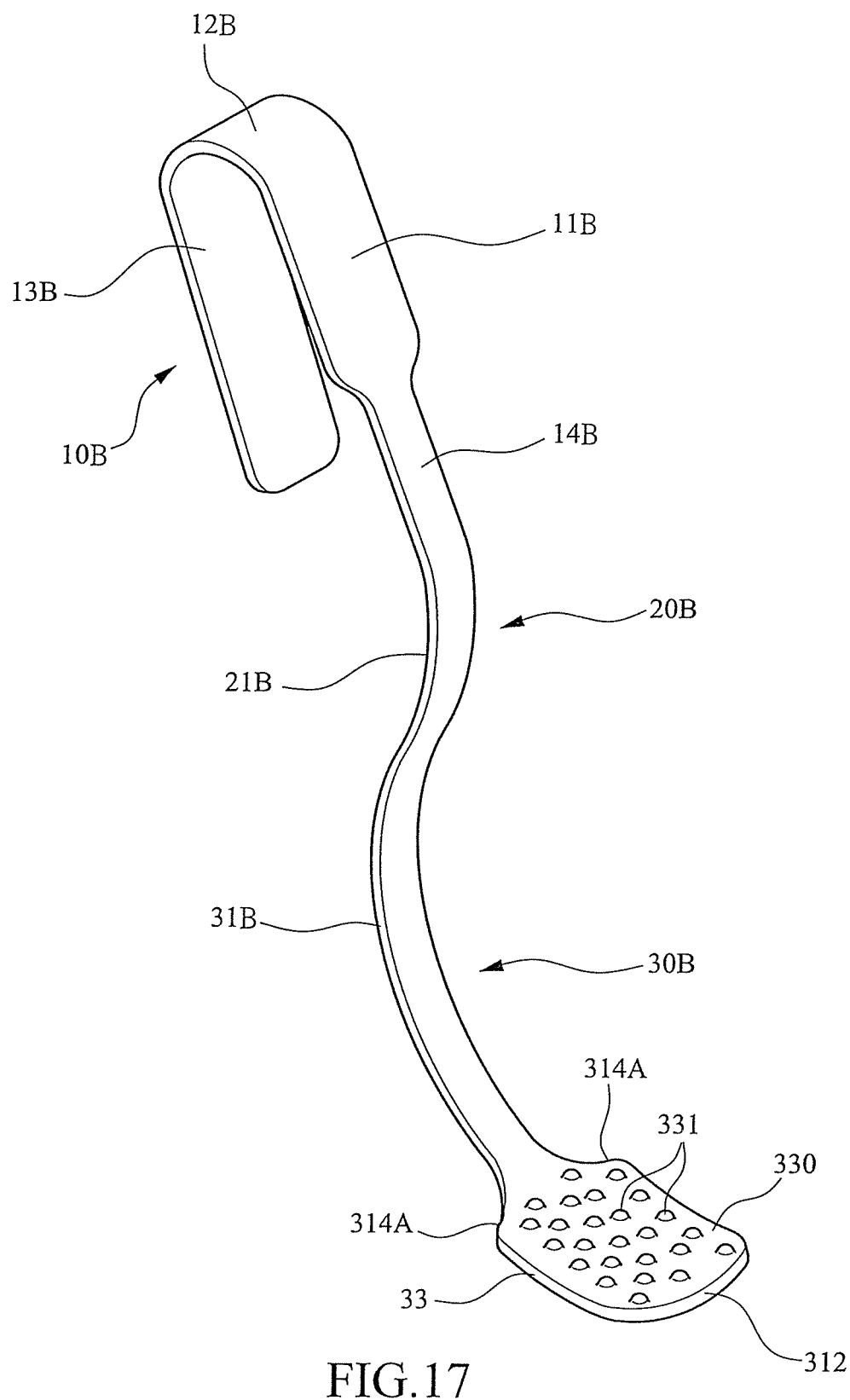
FIG. 17 is a perspective view of a tongue anteriorizer according to a ninth preferred embodiment of the invention.

Referring to FIG. 17, a tongue anteriorizer in accordance with a ninth preferred embodiment of the invention is shown. The characteristics of the ninth preferred embodiment are substantially the same as that of the fourth preferred embodiment except the following. The handle 10B, the connecting part 20B and the tongue lifting part 30B are formed together by a plurality of narrower width portions wherein a wider portion 11B and a narrower portion 14B are formed for the handle 10B, a narrower portion 21B is form for the connecting part 20B and the upper narrower portion 31B and the lower wider portion 33 are formed for the curved portion 31B of the tongue lifting part 30B so that the width of the curved portion 31B of the tongue lifting part 30B and the narrower portion 21B of the connecting part 20B are changed their width narrower than that of the above embodiments. It is to be understood that the optimum values of the slightly flexible deformation of the above-mentioned narrower portions for operating the tongue anteriorizer of the invention are provided for the particular patient.

Figure 18:
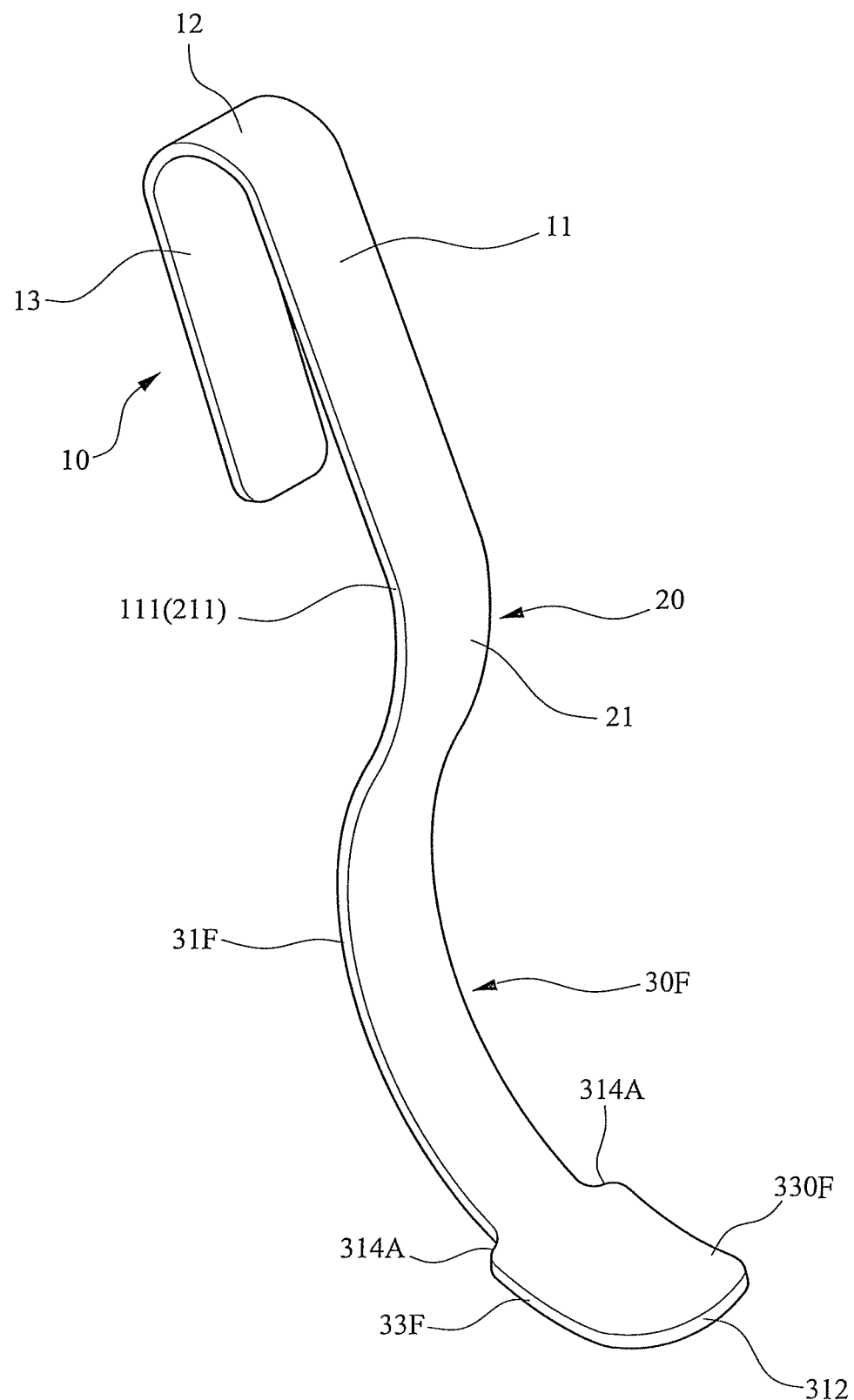
FIG. 18 is a perspective view of a tongue anteriorizer according to a tenth preferred embodiment of the invention.

Referring to FIG. 18, a tongue anteriorizer in accordance with a tenth preferred embodiment of the invention is shown. The characteristics of the tenth preferred embodiment are substantially the same as that of the fourth preferred embodiment, two opposite inclined shoulders 314A are formed between the enlargement 33F and the curved portion 31F of the tongue lifting part 30F, the width of the enlargement 33F is less than twice that of the connecting part 20, and no protrusions formed on the surface of the enlargement 33F.

Figure 19:
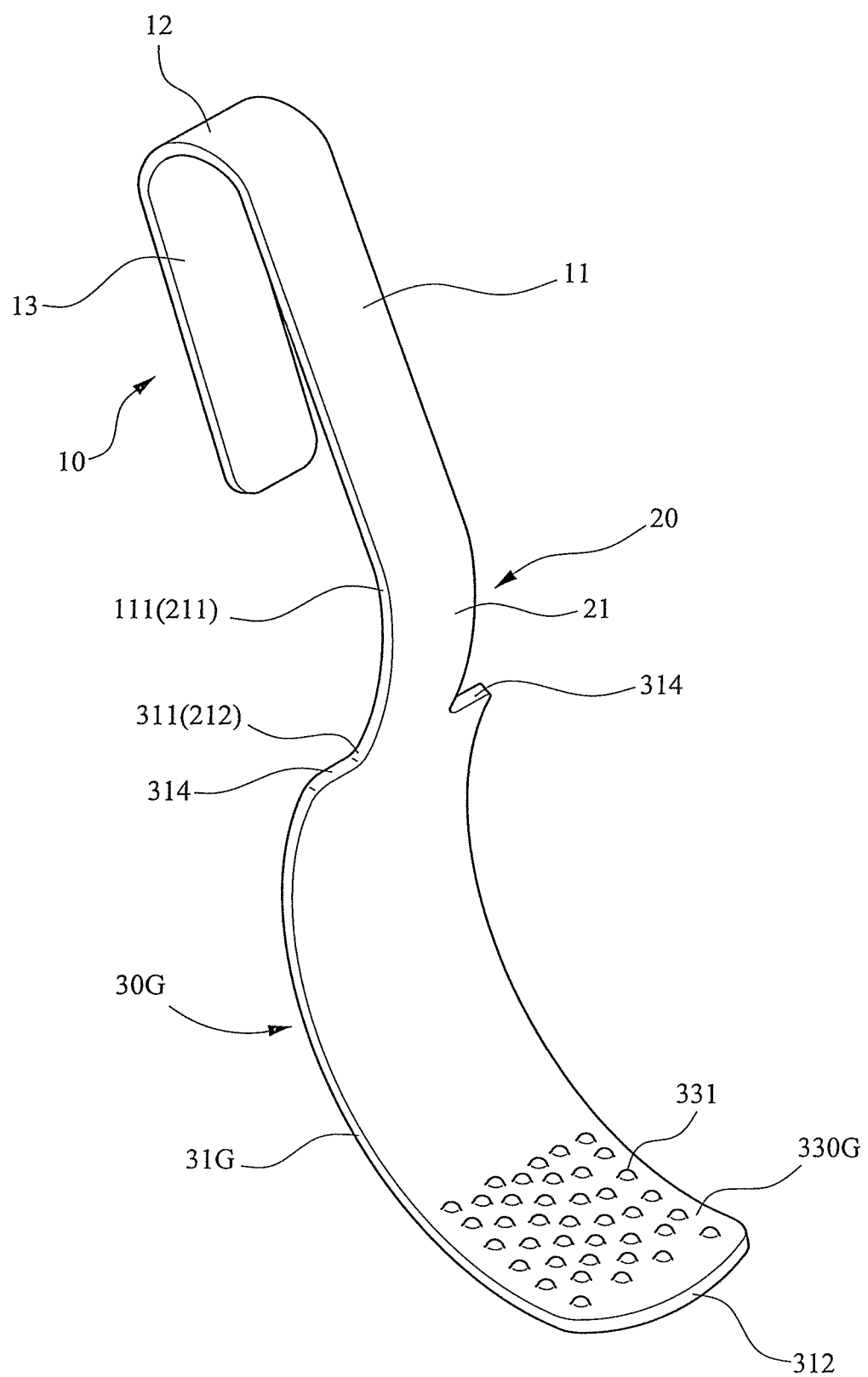
FIG. 19 is a perspective view of a first configuration of a tongue anteriorizer according to a eleventh preferred embodiment of the invention.
Figure 20:
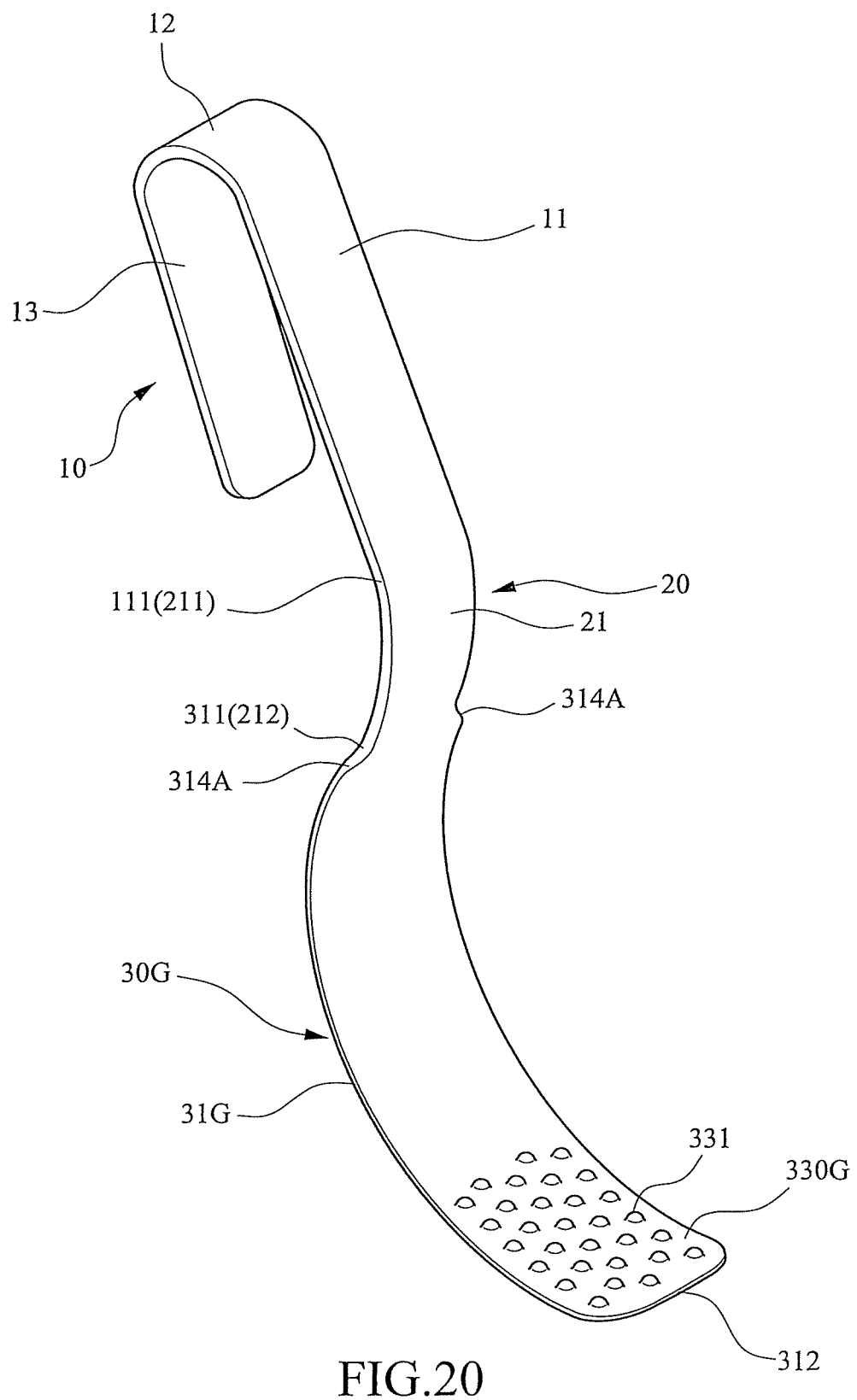
FIG. 20 is a perspective view of the second configuration of the tongue anteriorizer according to the eleventh preferred embodiment of the invention.

Referring to FIGS. 19 and 20, a tongue anteriorizer in accordance with a eleventh preferred embodiment of the invention is shown. The characteristics of the eleventh preferred embodiment are substantially the same as that of the third preferred embodiment except the following: In a first configuration, two opposite flat shoulders 314 are formed between the connecting member 21 of the connecting part 20 and the curved portion 31G of the tongue lifting part 30G, so that width of the curved portion 31G of the tongue lifting part 30G is greater than that of the connecting member 21 of the connecting part 20, the width of the curved portion 31G is less than twice that of the connecting part 20, and a plurality of protrusions 331 are formed on the front end portion of the long strip surface 330G of the curved portion 31G of the tongue lifting part 30G adjacent to the second end 312. In a second configuration, two opposite inclined shoulders 314A are formed between the connecting member 21 of the connecting part 20 and the curved portion 31G of the tongue lifting part 30G, so that width of the curved portion 31G of the tongue lifting part 30G is greater than that of the connecting member 21 of the connecting part 20, the width of the curved portion 31G is less than twice that of the connecting part 20, and a plurality of protrusions 331 are formed on the front end portion of the long strip surface 330G of the curved portion 31G of the tongue lifting part 30G adjacent to the second end 312.

It is envisaged by the invention that when the tongue, especially its base, can be moved anteriorly and lifted, there will be no difficult intubation. The tongue anteriorizer can move the tongue anteriorly, open the laryngopharyngeal area, and make all endotracheal intubation simple, safe, easy and efficient.

It is further noted that a method of operating a tongue anteriorizer of the invention comprises a handle and a tongue lifting part having an arc member, comprising the steps of:

(1) holding the handle and inserting the arc member of the tongue lifting part into a mouth of a patient until it reaching a base of a posterior part of the tongue;

(2) hooking the posterior part of the tongue by a front end of the arc member, lifting the tongue, and pulling the handle in a direction out of the mouth to cause the arc member of the tongue lifting part to exert force on the tongue; and (3) pulling the tongue by the tongue lifting part to move anteriorly along the top surface of the tongue.

While the invention has been described in terms of various embodiments, those skilled in the art will recognize that the invention can be practiced with modifications within the scope of the appended claims.

What is claimed is:

1. A tongue anteriorizer having a first device end and a second device end, said tongue anteriorizer comprising:
a handle on the first device end;
a connecting part comprising a curved connecting member having a first connecting end and a second connecting end, the first connecting end formed with the handle, the connecting part having a connecting part width, and
a tongue lifting part on the second device end, the tongue lifting part including an arc member having a first member end and a second member end, the first member end formed with the second connecting end of the curved connecting member, wherein the arc member comprises a wider section having a section width greater than the connecting part width;
wherein the handle comprises a curved handle section and a straight handle end between the curved handle section and the first connecting end of the curved connecting member;
wherein the arc member is shaped as a section of a circle or a section of an ellipse, and having a subtense defined by a straight line joining the first member end and the second member end of the arc member;
wherein the straight handle end and the subtense form an angle away from the arc member defining an angular relationship between the straight handle end and the arc member, and the angle is in a range between 90 degrees and 210 degrees; and
wherein the curved connecting member comprises a curve oriented in a direction opposite to a curved direction of the arc member.

2. The tongue anteriorizer according to claim 1, wherein the section width of the wider section is smaller than twice the connecting part width.

3. The tongue anteriorizer according to claim 1, wherein a curved length of the connecting part is less than one-third of a curved length of the arc member.

4. The tongue anteriorizer according to claim 1, wherein the tongue anteriorizer is made of a flat plate-like strip having a uniform thickness bent only in one direction.

5. The tongue anteriorizer according to claim 1, wherein the wider section of the arc member has a plurality of protrusions.

6. The tongue anteriorizer according to claim 1, wherein the wider section is near the second open end of the arc member.

7. The tongue anteriorizer according to claim 1, wherein the wider section extends from the second open end to the first member end of the arc member.

8. The tongue anteriorizer according to claim 5, wherein the wider section is near the second open end of the arc member.

9. The tongue anteriorizer according to claim 5, wherein the wider section extends from the second open end to the first member end of the arc member.

10. The tongue anteriorizer according to claim 1, wherein the wider section of the arc member is near the second open end of the arc member, the arc member further having a narrower section narrower than the wider section, the narrower section extends from the wider section to the first member of the arc member, the narrower section having a width smaller than the connecting part width.

11. The tongue anteriorizer according to claim 1, wherein the wider section of the arc member is near the second open end of the arc member, the arc member further having a narrower section narrower than the wider section, the narrower section extends from the wider section to the first member of the arc member, the narrower section having a width equal to the connecting part width.

12. The tongue anteriorizer according to claim 1, wherein the handle has a first handle end and a second handle end, the first handle end having a curved section and the second handle end formed with the second connecting end of the curved connecting member.

13. The tongue anteriorizer according to claim 1, wherein the subtense has a length and the arc member has a depth defined by a maximum distance between the subtense and the section of said circle or the section of said ellipse, and wherein the depth is ¼ to ½ the length of the subtense.

14. The tongue anteriorizer according to claim 13, wherein the length of the subtense is 5 to 9 cm.

* * * * *